United States Patent
Kassem et al.

(10) Patent No.: US 10,271,798 B2
(45) Date of Patent: Apr. 30, 2019

(54) METHODS, SYSTEMS, AND DEVICES FOR MONITORING AND DISPLAYING MEDICAL PARAMETERS FOR A PATIENT

(71) Applicant: DePuy Synthes Products, Inc., Raynham, MA (US)

(72) Inventors: Salim Kassem, North Attleboro, MA (US); Nicholas Baruch, North Smithfield, RI (US)

(73) Assignee: Integra Lifesciences Corporation, Plainsboro, NJ (US)

( * ) Notice: Subject to any disclaimer, the term of this patent is extended or adjusted under 35 U.S.C. 154(b) by 0 days.

(21) Appl. No.: 15/674,800

(22) Filed: Aug. 11, 2017

(65) Prior Publication Data

US 2017/0340294 A1 Nov. 30, 2017

Related U.S. Application Data

(63) Continuation of application No. 13/804,669, filed on Mar. 14, 2013, now Pat. No. 9,730,648.

(51) Int. Cl.
*A61B 5/03* (2006.01)
*A61B 5/00* (2006.01)
(Continued)

(52) U.S. Cl.
CPC .............. *A61B 5/7425* (2013.01); *A61B 5/01* (2013.01); *A61B 5/021* (2013.01); *A61B 5/0205* (2013.01);
(Continued)

(58) Field of Classification Search
CPC ....... A61B 5/742; A61B 5/031; A61B 5/7275; A61B 5/746; A61B 5/7425
See application file for complete search history.

(56) References Cited

U.S. PATENT DOCUMENTS

| 4,651,746 A | 3/1987 | Wall |
| 5,121,470 A | 6/1992 | Trautman |

(Continued)

FOREIGN PATENT DOCUMENTS

| JP | 2003513693 A | 4/2003 |
| JP | 2004129788 A | 4/2004 |

(Continued)

OTHER PUBLICATIONS

U.S. Appl. No. 13/803,667, filed Mar. 14, 2013. (70 pages).

(Continued)

*Primary Examiner* — Eric D. Bertram
(74) *Attorney, Agent, or Firm* — Mintz Levin Cohn Ferris Glovsky and Popeo, P.C.

(57) ABSTRACT

Methods, systems, and devices are provided for monitoring and displaying medical parameters for a patient. In one embodiment, a display can be configured to show a display screen that includes information related to a physiological parameter being measured from a patient. The information can include trends of values of the physiological parameter gathered from the patient over a period of time. The display screen can also show assessment information regarding one or more diagnostic parameters for the patient and notification information regarding one or more medically-related events that occurred as related to the patient. The trends information, the assessment information, and the notification information can be shown on the display screen alone or in any combination.

12 Claims, 18 Drawing Sheets

(51) Int. Cl.
*A61B 5/0205* (2006.01)
*A61B 5/01* (2006.01)
*A61B 5/021* (2006.01)
*A61B 5/1455* (2006.01)
*G16H 40/63* (2018.01)
*G06F 19/00* (2018.01)

(52) U.S. Cl.
CPC .......... *A61B 5/02055* (2013.01); *A61B 5/031* (2013.01); *A61B 5/14551* (2013.01); *A61B 5/743* (2013.01); *A61B 5/746* (2013.01); *A61B 5/7435* (2013.01); *G06F 19/00* (2013.01); *G16H 40/63* (2018.01)

(56) References Cited

U.S. PATENT DOCUMENTS

| | | |
|---|---|---|
| 5,226,416 A | 7/1993 | Bethune et al. |
| 5,262,944 A | 11/1993 | Weisner et al. |
| 5,285,792 A | 2/1994 | Sjoquist et al. |
| 5,438,983 A | 8/1995 | Falcone |
| 5,464,012 A | 11/1995 | Falcone |
| 5,522,387 A | 6/1996 | Simons |
| 5,785,043 A | 7/1998 | Cyrus et al. |
| 5,891,046 A | 4/1999 | Cyrus et al. |
| 5,920,263 A | 7/1999 | Huttenhoff et al. |
| 5,951,485 A | 9/1999 | Cyrus et al. |
| 6,241,661 B1 | 6/2001 | Schluess et al. |
| 6,305,373 B1 | 10/2001 | Wallace et al. |
| 6,322,502 B1 | 11/2001 | Schoenberg et al. |
| 8,027,846 B2 | 9/2011 | Schoenberg et al. |
| 8,764,672 B2 * | 7/2014 | Manwaring ............ A61B 5/027 600/506 |
| 9,636,070 B2 | 5/2017 | Kassem et al. |
| 9,730,648 B2 * | 8/2017 | Kassem ................ A61B 5/743 |
| 2002/0138512 A1 | 9/2002 | Buresh et al. |
| 2006/0064136 A1 | 3/2006 | Wang |
| 2009/0005703 A1 * | 1/2009 | Fasciano ................ A61B 5/031 600/561 |
| 2009/0113295 A1 | 4/2009 | Halpern et al. |
| 2009/0222065 A1 * | 9/2009 | Dlugos, Jr. ............. A61B 5/03 607/60 |
| 2009/0231341 A1 | 9/2009 | Lord et al. |
| 2009/0275807 A1 | 11/2009 | Sitzman et al. |
| 2010/0081891 A1 | 4/2010 | Wang et al. |
| 2011/0040701 A1 | 2/2011 | Singla et al. |
| 2011/0040713 A1 | 2/2011 | Colman et al. |
| 2011/0218406 A1 | 9/2011 | Hussain |
| 2014/0022256 A1 * | 1/2014 | Carnes ................ A61B 5/02416 345/440.1 |
| 2014/0275819 A1 | 9/2014 | Kassem et al. |

FOREIGN PATENT DOCUMENTS

| | | |
|---|---|---|
| JP | 2004248793 A | 9/2004 |
| JP | 2008531209 A | 8/2008 |
| JP | 2008200111 A | 9/2008 |
| JP | 2011147493 A | 8/2011 |
| WO | WO-03091841 A2 | 11/2003 |
| WO | 2006077798 A1 | 7/2006 |
| WO | WO-2011002904 A2 | 1/2011 |
| WO | WO-2014047171 A1 | 3/2014 |

OTHER PUBLICATIONS

U.S. Appl. No. 13/804,669, filed Mar. 14, 2013, now U.S. Pat. No. 9,730,648, Methods, systems, and devices for monitoring and displaying medical parameters for a patient.

Japanese Office Action for Application No. 2014-050106, dated Jan. 30, 2018 (5 pages).

* cited by examiner

METHODS, SYSTEMS, AND DEVICES FOR MONITORING AND DISPLAYING MEDICAL PARAMETERS FOR A PATIENT

CROSS REFERENCE TO RELATED APPLICATIONS

The present application claims priority to U.S. patent application Ser. No. 13/804,669 entitled "Methods, Systems, and Devices for Monitoring and Displaying Medical Parameters for a Patient" filed Mar. 14, 2013, now U.S. Pat. No. 9,730,648, which is hereby incorporated by reference in its entirety.

FIELD

The present disclosure relates generally to methods, systems, and devices for monitoring and displaying medical parameters for a patient.

BACKGROUND

Patient monitoring can take a variety of forms and can gather a wide variety of physiological data. The display of such data, including what is displayed and how it is displayed, can affect the ability of caregivers, such as doctors and nurses, to interpret and act on the data. For example, intracranial pressure (ICP) is a standard monitoring modality for traumatic brain injury patients. Medical guidelines may prescribe threshold values for intracranial pressure. The guidelines of the Brain Trauma Foundation, for example, indicate that clinical action should be taken to reduce intracranial pressure if the intracranial pressure exceeds 20-25 mmHg. However, numerous factors can cause transient changes to intracranial pressure, including patient physiology, monitoring system noise, and actions taken by a caregiver.

To monitor a patient, caregivers typically use monitoring devices such as the Codman ICP Express device 100, which is shown in FIG. 1, available from Codman & Shurtleff, Inc. of Raynham, Mass. As shown, the device 100 has a display of intracranial pressure and a display of systolic and diastolic values for the intracranial pressure, as well as an alarm. A caregiver can look at the display to ascertain the intracranial pressure. Caregivers also use charts, e.g., a caregiver can manually record an event in a chart associated with a patient.

One drawback with current monitoring devices is that the devices only provide a limited amount of patient data. Caregivers thus only have a limited picture of a patient's condition from a monitoring device on which to base decision making regarding treatment of the patient. It can therefore be difficult for caregivers to make clinical decisions based on the patient data displayed on a monitoring device without taking additional time to review other patient records, e.g., paper files. Taking this additional time can adversely affect patient treatment, particularly in critical care situations, such as situations involving traumatic brain injury patients, where treatment delays can greatly exacerbate injuries or otherwise be particularly problematic. Moreover, such considerations are applicable not just to intracranial pressure, but to a wide variety of patient monitoring modalities involving other physiological parameters.

Accordingly, there remains a need for improved methods, systems, and devices for monitoring and displaying medical parameters for a patient.

SUMMARY

Methods, systems, and devices are provided for monitoring and displaying medical parameters for a patient. In one embodiment, a system is provided that includes a display screen and a processor. The processor is configured to receive a plurality of values for each of a plurality of physiological parameters measured from a patient over a period of time and cause a plurality of windows to be displayed on the display screen. The plurality of windows include a current value window that shows a current value for each of the plurality of physiological parameters, and a trends window that shows a trendline for each of the plurality of physiological parameters. Each of the trendlines indicates for its associated physiological parameter the values of the physiological parameter over the period of time. The processor is also configured to cause a time marker to be displayed on the trends window. A position of the time marker relative to each of the trendlines indicates a selected time within the period of time. The processor is also configured to cause an assessment window to be displayed on the display screen that indicates a value of each of the plurality of physiological parameters at the selected time.

The system can vary in any number of ways. For example, the marker can be movable simultaneously along each of the trendlines. For another example, the processor can be configured to allow a user to select which one or more of the plurality of physiological parameters to be concurrently displayed in the trends window. For yet another example, the processor can be configured to cause a detail trends window to be displayed on the display screen in response to a user selecting any one of the trendlines at the position of the time marker. The detail trends window can show a more detailed version of a portion of the selected trendline for a second period of time including the selected time. The second period of time can be less than the period of time. For another example, the processor can be configured to display the assessment window concurrently with the trends window on the display screen, or the processor can be configured to only display the assessment window concurrently with the trends window on the display screen in response to a user input to the processor. For still another example, the processor can be configured to concurrently display each of the plurality of windows on the display screen. For another example, the processor can be configured to display a selected one or more of the plurality of windows at a time. The displayed one or more windows can be user selected from among the plurality of windows. For another example, the processor can be configured to allow a user to repeatedly change a length of the period of time. For yet another example, the plurality of windows can include a future window that displays projected future values for each of the physiological parameters values beyond the time period. The processor can be configured to calculate the projected future values based on the measured values.

The plurality of physiological parameters can include at least two of intracranial pressure (ICP), cerebral perfusion pressure (CPP), mean arterial blood pressure (MAP), oxygen saturation ($pO_2$), heart rate, and temperature.

In some embodiments, the processor can be configured to cause a notification marker to be shown on the trends window. The notification marker can be disposed at a point within the period of time that corresponds to a time at which a medically-related event occurred related to the patient. The notification marker can be configured to be manually input by a user, or the notification marker can be configured to be automatically added in response to an automatically occurring event.

In another aspect, a method is provided that in one embodiment includes receiving a plurality of values for each of a plurality of physiological parameters measured from a patient over a period of time and displaying a plurality of windows on a display screen. The plurality of windows include a current value window that shows a current value for each of the plurality of physiological parameters, and a trends window that shows a trendline for each of the plurality of physiological parameters. Each of the trendlines indicates for its associated physiological parameter the values of the physiological parameter over the period of time. The method also includes displaying a time marker on the trends window. A position of the time marker relative to each of the trendlines indicates a selected time within the period of time. The method also includes displaying an assessment window on the display screen that indicates a value of each of the plurality of physiological parameters at the selected time.

The method can have any number of variations. For example, the marker can be movable simultaneously along each of the trendlines. For another example, the method can include showing a notification marker on the trends window. The notification marker can be disposed at a point within the period of time that corresponds to a time at which a medically-related event occurred related to the patient. The notification marker can be configured to be manually input by a user or to be automatically added in response to an automatically occurring event.

The plurality of physiological parameters can include at least two of ICP, CPP, MAP, pO$_2$, heart rate, and temperature.

In another aspect, a tangible computer readable medium is provided that has stored thereon a program. The program can, when executed, perform the method.

BRIEF DESCRIPTION OF DRAWINGS

This invention will be more fully understood from the following detailed description taken in conjunction with the accompanying drawings, in which.

DETAILED DESCRIPTION

Figure 1:
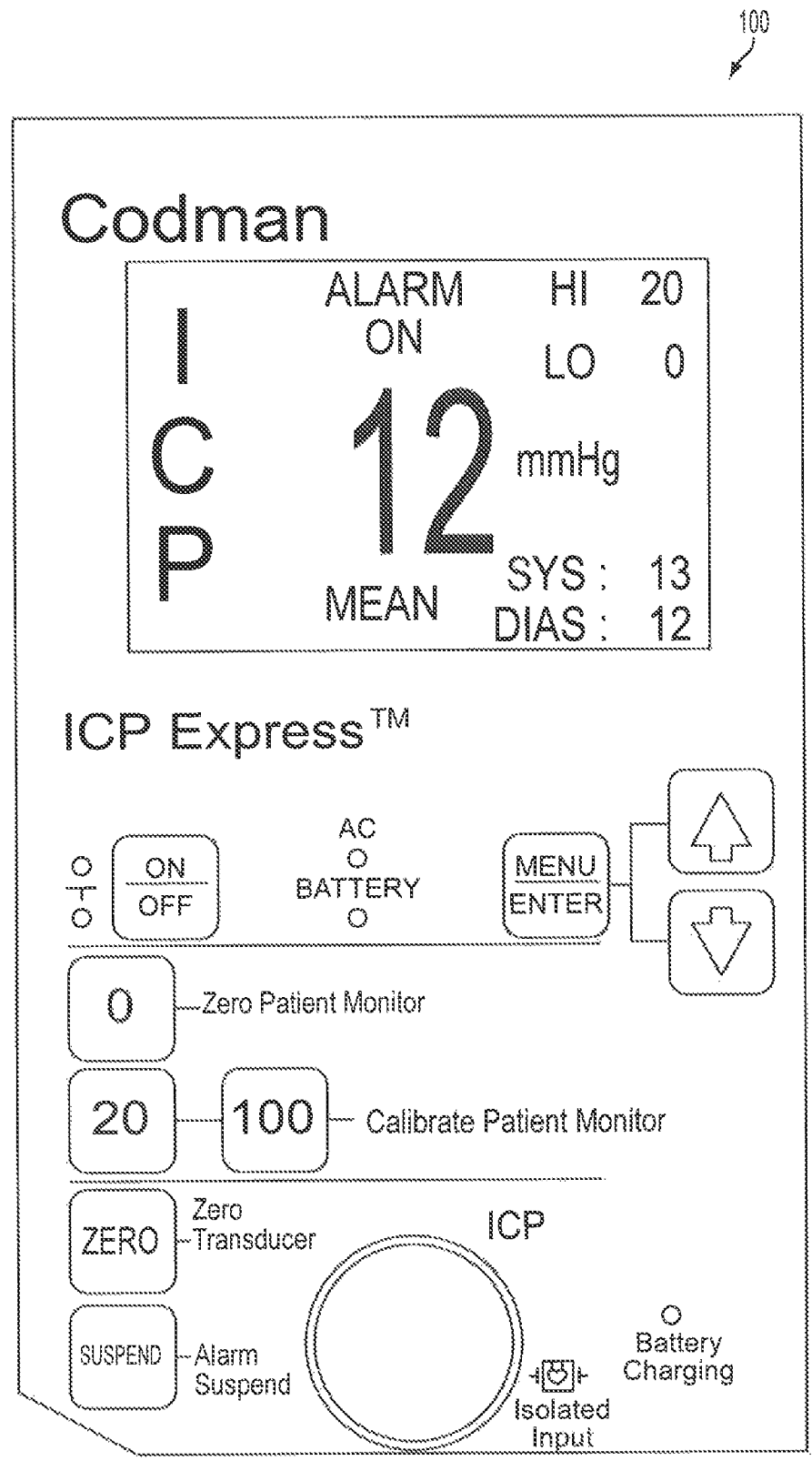
FIG. 1 (PRIOR ART) is a schematic diagram of a monitoring device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Methods, systems, and devices are provided for monitoring and displaying medical parameters for a patient. In general, the methods, systems, and devices can facilitate monitoring of a patient, such as when the patient is being treated at a hospital or other medical facility at which the patient's condition can require regular observation. The methods, systems, and devices can allow the displaying and monitoring of one or more physiological parameters of the patient. This monitoring and display can facilitate identification of changes in the patient's condition that may require a doctor's assessment and/or may require an adjustment of the patient's treatment, e.g., administration of medication(s), administration of oxygen, adjustment of one or more settings of an implanted medical device, adjustment of an elevated limb's position, additional hydration, movement to another hospital unit, etc. Generally, as will be appreciated by a person skilled in the art, the earlier the change in the patient's condition can be detected, the more time medical personnel can have to assess and effectively address the change. The methods, systems, and devices described herein can facilitate quick detection and identification of changes in the patient's condition, thereby facilitating quick, effective treatment of the patient.

In one embodiment, a display can be configured to show a display screen that includes information related to a physiological parameter being measured from a patient. The information can include trends of values of the physiological parameter gathered from the patient over a period of time. The display screen can simultaneously display trends for a plurality of physiological parameters, thereby facilitating comparison of the parameters and evaluation of the patient's condition. Which of the physiological parameters' trends are displayed at the same time on the display screen can be selectively adjusted, thereby facilitating comparison of different parameters with one another. The display screen can also show assessment information regarding one or more diagnostic parameters for the patient and notification information regarding one or more medically-related events that occurred as related to the patient. The trends information, the assessment information, and the notification information can be shown on the display screen alone or in any combination. When the assessment information is shown on the display screen simultaneously with the trends information, the assessment information and the trends information can each be time-aligned with one another on the display screen. This time alignment can facilitate identification of reasons for any changes in the various trends. Similarly, when the notification information is shown on the display screen simultaneously with the trends information, the notification information and the trends information can each be time-aligned with one another on the display screen, which can facilitate identification of reasons for any changes in the various trends.

The physiological parameters can include any one or more variables that can be monitored from a patient, as will be appreciated by a person skilled in the art. If a display screen shows current values for a plurality of physiological parameters, the display screen can indicate whether or not each one of the physiological parameters is within its own predetermined range, e.g., can trigger an alarm if any one of the physiological parameters falls outside its associated predetermined range. The one or more physiological parameters monitored from a patient can vary due to one or more factors such as medical context (e.g., neurological, cardiac, neonatal, etc.), available supplies, doctor preference, etc. Examples of physiological parameters include intracranial pressure (ICP), mean arterial blood pressure (MAP), cerebral perfusion pressure (CPP), oxygen saturation (pO$_2$) (which can be obtained by, e.g., using an invasive oxygen sensor or a pulse oximeter) such as oxygen saturation in brain tissue (PbO2), heart rate, temperature, pressure reactivity index (PRx), pressure-volume compensatory reserve (RAP) index, fluid pressure in an implantable restriction device (e.g., a gastric band, etc.), flow rate through an implantable valve (e.g., a cerebral shunt valve, etc.), gastric pH level, EEG, tissue impedance, etc. In a neurological context, exemplary monitored physiological parameters include ICP, CPP, MAP, PbO2, heart rate (HR), and brain temperature (Tb).

The displays described herein can be realized as part of virtually any device, e.g., a monitoring device, a personal computer, a workstation, a handheld computer, a tablet computer, a smartphone, or other computing device. The device can include processing circuitry configured to receive data from one or more sensors configured to gather physiological data from a patient, configured to compare sensor data to stored predetermined ranges, etc. A wide variety of displays, such as cathode ray tubes (CRTs), liquid crystal display (LCD) screens, touchscreens, etc., can be configured to display screens in response to a signal received from the processing circuitry, as a person skilled in the art will appreciate. Moreover, a wide variety of software packages can be executed on the device and/or used to develop the screens and other elements, including, for example, Flash Macromedia or custom software.

Figure 2:
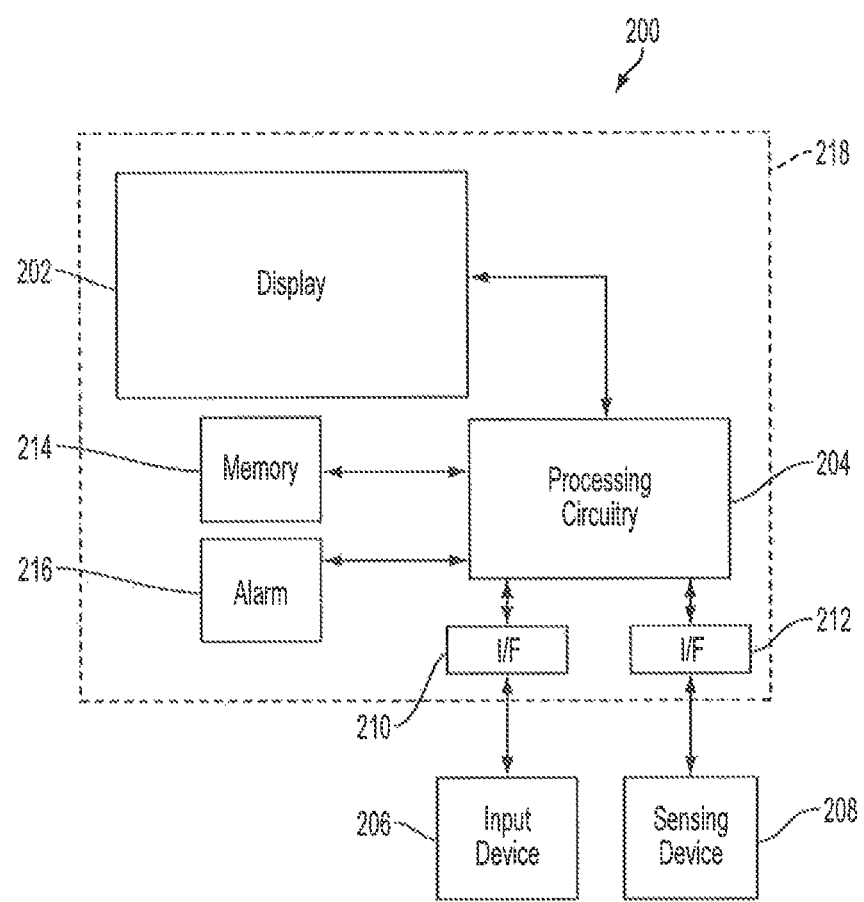
FIG. 2 is a schematic diagram of one embodiment of a device for providing a user interface on a display of the device.

FIG. 2 shows an exemplary embodiment of a device (e.g., a medical monitoring device) that can include a display screen configured to show information. The device 200 can include one or more displays 202 configured to show screens such as those described herein. The display(s) 202 can be configured to receive signals from processing circuitry 204, which can include a processor, a video card, and/or virtually any type of electronic circuitry. The processing circuitry 204 can be configured to execute software to draw appropriate screens in response to data from one or more input devices 206, e.g., representing user input, and/or data from one or more sensing devices 208. The input device(s) 206 can include devices configured to provide an input to the device 200 such as pointing devices, keyboards, buttons, microphones, soft-keys, touchscreens, etc. The input device(s) 206 can be configured to be communicatively coupled to the processing circuitry 204 via a device interface 210. The sensing device(s) 208 can include devices configured to sense and report on a physiological parameter. Examples of the sensing device(s) 208 include ICP transducers, temperature sensors, blood pressure monitors, pulse oximeters, evoked potentials, etc. The sensing device(s) 206 can be configured to be communicatively coupled to the processing circuitry 204 via a device interface 212. A memory 214 can be configured to be coupled to the processing circuitry 204 and be configured to store data, such as monitoring software, data from the sensing device(s) 208, predetermined ranges, patient data, etc. The device 200 can include an alarm mechanism 216 configured to providing an alarm, e.g., a visual alarm, an auditory alarm, a textual alarm, etc.

In an exemplary embodiment, a housing 218 of the device 200 can house, e.g., have disposed therein and/or have attached thereto, the display(s) 202, the memory 214, the alarm 216, the processing circuitry 204, and the interfaces 210, 212. In this way, the device 200 can be a self-contained unit. The device 200 can thus be portable, wireless, and/or easily connected to wired power supplies in a variety of different locations. The elements included in the housing 218 can vary. For example, although shown in FIG. 2 as separate devices, e.g., not included a housing 218 having the display(s) 202, the memory 214, the alarm 216, the processing circuitry 204, the interfaces 210, 212 disposed therein, the input devices 206 and sensing devices 208 can be integrated into the device 200, e.g., included the hosing 218.

Additionally, although the display(s) 202 are shown in FIG. 2 as being integrated with the device 200, e.g., attached to the housing 218, one or more of the display(s) 202 can be separate from the device 200.

Figure 3:
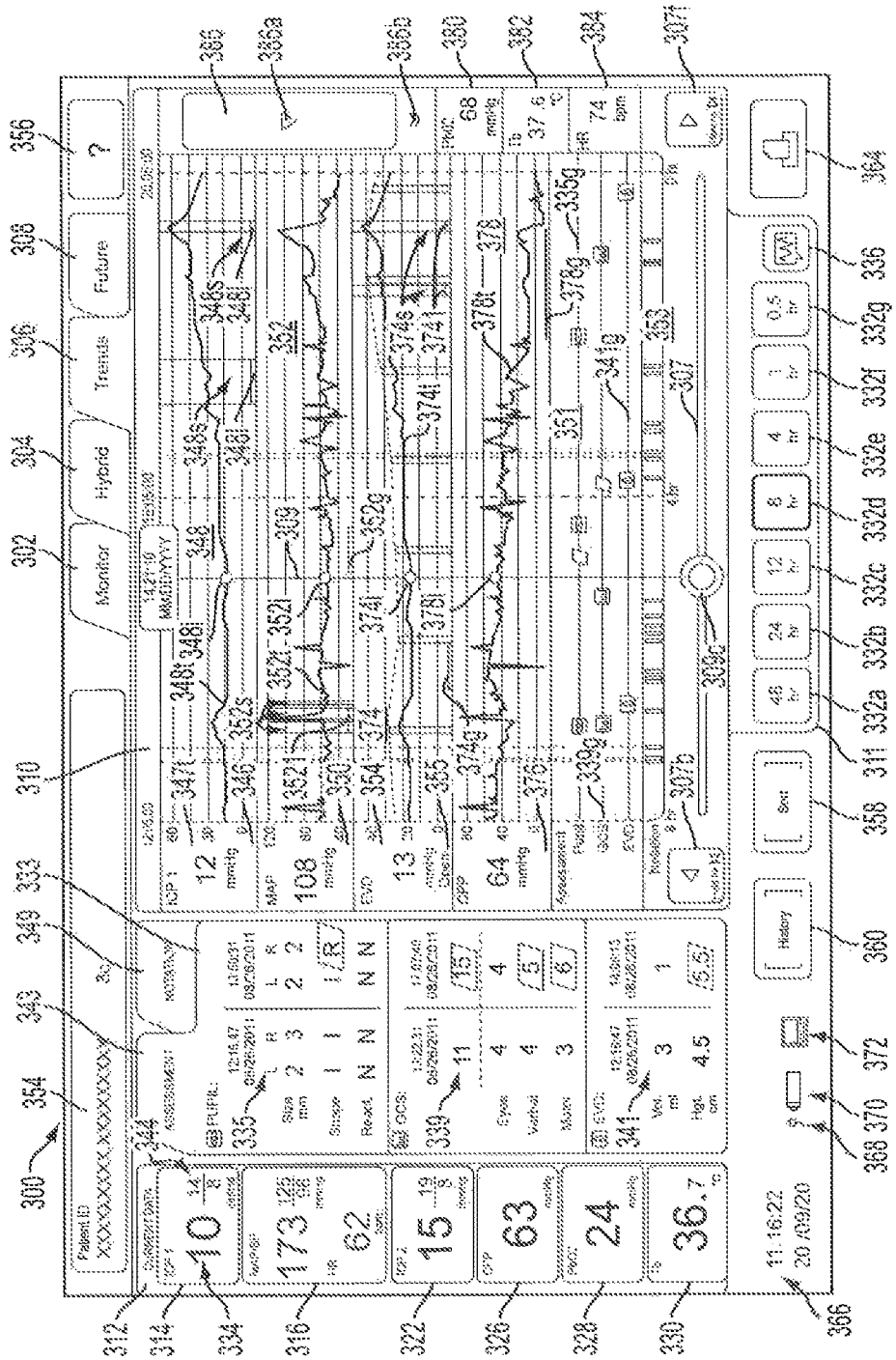
FIG. 3 is an embodiment of a trends window of a medical monitoring system, the trends window showing trends information over a trends period of time for a plurality of physiological parameters, current data over a current period of time for the plurality of physiological parameters, and assessment information over the trends period of time.

FIG. 3 shows an exemplary embodiment of a display screen 300 of a monitoring device configured to display medical information related to a patient. The display screen 300 can generally be configured as a user interface of a medical monitoring system. The display screen 300 can include a plurality of screen type tabs, each of the screen type tabs corresponding to a certain type or arrangement of information related to the patient. A display screen can be configured to only show one type or arrangement of information related to a patient, in which case the display screen can lack screen type tabs. Each of the screen type tabs can be configured to be selected by a user so as to display the screen type tab's corresponding type or arrangement of information. In the illustrated embodiment, the display screen 300 includes a monitor tab 302, a hybrid tab 304, a trends tab 306, and a future tab 308, but the display screen 300 can include more or less than four tabs. The trends tab 306 is selected in FIG. 3 so as to show a trends window 310 on the display screen 300. The monitor, hybrid, and future tabs 302, 304, 308 can each be selected so as to show, respectively, a hybrid window, a trends window, and a future window on the display screen 300, as discussed further below.

The display screen 300 can include a wide variety of other features and display a wide variety of other data. The display screen 300 can include one or more static features configured to be on the display screen 300 regardless of which of the tabs 302, 304, 306, 308 is currently selected. For example, the display screen 300 can include any one or more of a patient ID window 354 that identifies the patient (e.g., by name, number, code, etc.); a help button 356 configured to be user-activated so as to provide technical assistance (e.g., access to a user manual, ability to search Frequently Asked Questions, etc.); a sort button 358 configured to be user-activated so as to allow reordering of parameters shown on the currently displayed window (which is the trends window 310 in FIG. 3), which can be advantageous for comparing different selected ones of the parameters; a history button 360 configured to be user-activated so as to provide historical sensed data for the patient and/or other patient records; a print button 364 configured to be user-activated so as to provide the ability to print the currently displayed window or portion(s) thereof (e.g., print to an attached printer or a printer integrated into the medical monitoring device); a current date/time indicator 366; a power connector 368 that indicates whether or not the device is connected to external electrical power; a charge indicator 370 that indicates a current charge of a battery included in the monitoring device; a docking indicator 372 that indicates whether or not the device is docked at a docking station (e.g., a bedside docking station, etc.); etc. Embodiments of providing historical sensed data and embodiments of marking events are described in further detail in U.S. Pat. Pub. No. 2009/0005703 entitled "Medical Monitor User Interface" filed Jun. 27, 2007, which is hereby incorporated by reference in its entirety. One or more static features may only be shown on the trends window 310 in response to a trigger event, such as the charge indicator 370 being configured to appear only when the battery charge is low.

The relative sizes and locations of the various windows, symbols, text, icons, etc. of the trends window 310, and for other windows that can be shown on the display screen 300, are exemplary in nature. A person skilled in the art will appreciate that any of the various windows, symbols, text, icons, etc. of the display screen 300 can have virtually any size and virtually any location.

The current data window 312 can be configured to show current information for one or more physiological parameters. In the illustrated embodiment, the current data window 312 shows current information for ICP, MAP/BP, HR, external ventricular drainage (EVD) ICP (e.g., an ICP measurement performed with an external fluid coupled sensor that is connected to the EVD system) variously shown as "ICP 2" and "EVD," CPP, PbO2, and Tb, but as mentioned above, any one or more parameters can be monitored and/or calculated, and information for any one or more types of current values based on the physiological parameters can be shown on the current data window 312. The current information displayed for each of the physiological parameters can be based on data received by the monitoring device in any of a variety of ways, as will be appreciated by a person skilled in the art, e.g., via a Codman Microsensor ICP Transducer (available from Codman & Shurtleff, Inc. of Raynham, Mass.), via an Integra Camino® ICP Transducer (available from Integra LifeSciences Corporation of Plainsboro, N.J.), via a blood pressure monitor, via a temperature sensor attached to the patient, etc.

For each of the physiological parameters, the current data window 312 can be configured to show a textual display of current parameter information and/or a graphical display of current parameter information. In the illustrated embodiment, the current data window 312 includes an ICP textual display 314, a MAP/BP textual display 316, an HR textual display 318, a textual display 322 for EVD ICP, a textual display 326 for CPP, a textual display 328 for pbO2, and a textual display 330 for Tb. Which one or more of the physiological parameters have a textual display only, have a graphical display only, or have both a textual display and a graphical display can be user-adjusted, such as by dragging and dropping displays on the touchscreen.

The textual display of current information for each physiological parameter can include numerical data regarding the physiological parameter for a current time period, and the graphical display for each physiological parameter can include a graphical illustration of the numerical data for the current time period. The current time period can be a predetermined amount of time that can be a default, preprogrammed time period, e.g., preprogrammed into a processor, or can be customized for a particular patient. The current time period can be, e.g., in a range of about five to sixty seconds, in a range of about five to ten seconds, a single heartbeat, the most recent few heartbeats of the patient, etc. The current time period can be adjustable. In some embodiments, to receive user input of this nature, the medical monitoring device can include or be configured to couple to an input device, such as a touchscreen, keypad, touchpad, pointing device, mouse, button, knob, dial, etc. The display screen 300 can include a touchscreen configured to allow the current time period to be adjusted when, e.g., a user activates a main menu button, activates one of the textual displays included in the current data window 312 as discussed further below, etc. Adjustment of the current time period can allow for various clinical protocols, as such protocols that can require tracking of a parameter over different time periods. Trend time periods, future time periods, normal ranges, and goal ranges for the various physiological parameters, discussed further below, can be similarly adjusted.

For ease of discussion, the textual display 314 for ICP is discussed below as a representative example of a textual display for a physiological parameter shown in the current data window 312. Textual displays for other physiological parameters shown in the current data window 312 can be similarly configured. Additionally, ICP is shown in the current data window 312 in units of mmHg, but ICP can be displayed on any window in any appropriate unit. Similarly, other physiological parameters can be displayed in any appropriate units.

The textual display 314 can represent ICP textually and/or pictorially. In the illustrated embodiment, the textual display 314 includes a current value based on the received ICP values. The current value includes an average of ICP values gathered during the current time period including a current average (e.g., the current average intracranial pressure) and a goal range for the current average. Examples of current values include an average of gathered values, an average of a calculated index (e.g., an average of peak gathered values, an average of a rate of change of the gathered values, etc.), a median of gathered values, a rate of change of gathered values, a correlation (e.g., PRx, pressureRAP index, autocorrelation, an average of autocorrelation, etc.), a maximum value among the gathered values, a minimum value among the gathered values, a root mean square (RMS), peak-to-peak values, etc. Various embodiments of displaying current information related to physiological parameters are discussed in further detail in U.S. application Ser. No. 13/803,667 entitled "Methods, Systems, And Devices For Monitoring And Displaying Medical Parameters For A Patient" filed on Mar. 14, 2013, which is hereby incorporated by reference in its entirety.

The current value can be shown textually and/or graphically. In the illustrated embodiment, the current average is shown textually with a numerical value 334. The average ICP value in the illustrated embodiment is 10 mmHg. As will be appreciated by a person skilled in the art, the numerical value 334 shown on the trends window 310 can be an exact average value or can be a rounded value, e.g., rounded to a nearest whole number (as in the illustrated embodiment), rounded to one decimal place, rounded to two decimal places, etc.

The goal range can be shown textually and/or graphically. In the illustrated embodiment, the goal range is shown textually with an upper goal limit that corresponds to a predetermined upper limit of the goal range and with a lower goal limit that corresponds to a predetermined lower limit of the goal range. By way of example, a predetermined goal range for ICP can be about 5 to 15 mmHg, a predetermined goal range for CPP can be about 70 to 90 mmHg, a predetermined goal range for Tb can be about 36.5 to 37.1° C., and a predetermined goal range for MAP can be about 80 to 100 mmHg. In the illustrated embodiment, the upper goal limit for ICP is 14 mmHg, and the lower goal limit for ICP is 8 mmHg; the upper goal limit for MAP/BP is 125 mmHg, and the lower goal limit for MAP/BP is 98 mmHg; and the upper goal limit for EVD ICP is 19 mmHg, and the lower goal limit for EVD ICP is 8 mmHg. Goal ranges may not be displayed for one or more physiological parameters, such as if goal ranges have not yet been input for those parameter(s). Various embodiments of goal ranges for physiological parameters are discussed in further detail in U.S. application Ser. No. 13/803,667 entitled "Methods, Systems, And Devices For Monitoring And Displaying Medical Parameters For A Patient" filed on Mar. 14, 2013.

The current data window 312 can include a menu feature configured to facilitate changing system preferences such as time period adjustments, whether to show textual and/or graphical displays for a particularly physiological parameter, to adjust a predetermined normal range for a particular physiological parameter, to start or stop data collection from a sensing device associated with a physiological parameter, etc. By way of example, a typical normal range for ICP is about 0 to 20 mmHg, a typical normal range for CPP is about 50 to 150 mmHg, a typical normal range for Tb is about 36 to 37.5° C., and a typical normal range for MAP is about 70 to 110 mmHg. In one embodiment, the menu feature can include a menu button (not shown) configured to be user-activated, e.g., touched on a touchscreen, clicked on using a pointing device, etc. In another embodiment, each of the textual displays 314, 316, 318, 322, 326, 328, 330 for ICP, MAP/BP, HR, EVD ICP, CPP, pbO2, and Tb, respectively, can be configured as a user-selectable button, e.g., a button configured to be user-activated. Selecting one of the textual displays 314, 316, 318, 322, 326, 328, 330 in the current data window 312 can cause a preferences window to appear for the physiological parameter associated with the selected one of the textual displays 314, 316, 318, 322, 326, 328, 330.

Figure 4:
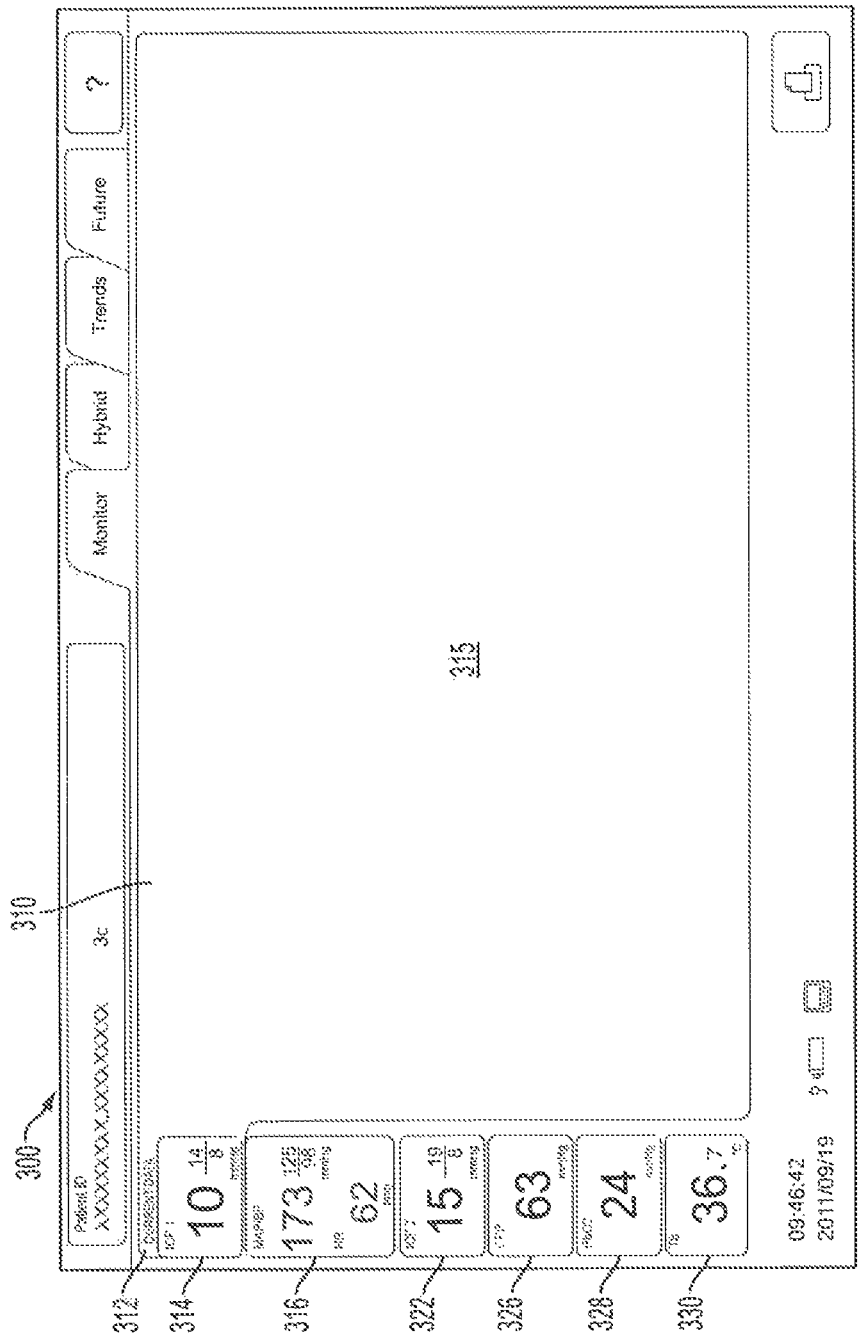
FIG. 4 is an embodiment of a preferences window of the system of FIG. 3.

FIG. 4 shows an embodiment of a preferences window 313 that can be configured to appear upon selection of one of the textual displays 314, 316, 318, 322, 326, 328, 330 in the current data window 312. In this illustrated example, the textual display 314 for ICP has been selected. The preferences window 313 can have a variety of configurations to facilitate changing various settings, as will be appreciated by a person skilled in the art. For example, various changeable settings (not shown) can appear in a body 315 of the preferences window 313 using any one or more preference settings mechanisms, e.g., text entry fields, selectable radio buttons, check boxes, etc.

Referring again to FIG. 3, the trends window 310 can be configured to show information for one or more physiological parameters in a trend time period. In an exemplary embodiment, the trend time period can be longer than the current time period, e.g., fifteen minutes, thirty minutes, ninety minutes, one hundred minutes, etc., although virtually any time period can be used as the trend time period. In some embodiments, the trend time period can be hours, days, or longer. The trend time period can entirely precede the current time period or can overlap at least partially with the current time period. In some embodiments, the trend time period can correspond to requirements of a particular physiological parameter. For example, the trend time period can correspond to a time period pertinent to ICP monitoring and thereby allow a caregiver to review this trend time period. Similar to that discussed above regarding the current time period, the trend time period can be a predetermined amount of time that can be a default, preprogrammed time period, e.g., preprogrammed into a processor, or can be customized for a particular patient.

The trend time period can be adjustable similar to that discussed above with respect to the current time period. The display screen 300 can include a trend time adjustment mechanism configured to facilitate user selection of a predetermined trend time period. In one embodiment, the trends window 310 can include a trend preferences button (not shown) configured to be activated to allow selection of the trend time period, such as by providing a preferences window in which different trend time periods can be selected. As in the illustrated embodiment, the trend time adjustment mechanism can include a trend time window 311 that be configured to include a plurality of selectable trend time buttons 332a, 332b, 332c, 332d, 332e, 332f, 332g. The trend time window 311 can be included as part of the trends window 306, as in the illustrated embodiment. The trend time window 311 can also include a detail time period button 336 configured to allow selection of a detail time period, discussed further below.

Each of the trend time buttons 332a, 332b, 332c, 332d, 332e, 332f, 332g can be configured to be user selected, such as when the display screen 300 is a touchscreen configured to allow a user to activate a selected one of trend time buttons 332a, 332b, 332c, 332d, 332e, 332f, 332g by touching the selected button. In the illustrated embodiment, an "8 hr" trend time button 332d is selected such that the trend time period in the embodiment of FIG. 3 is eight hours. The currently-selected trend time period can be identified on the trend window 310, such as by highlighting a selected one of the trend time buttons 332a, 332b, 332c, 332d, 332e, 332f, 332g, as in the illustrated embodiment in which the selected "8 hr" button 332d is a different color than a remainder of the trend time buttons 332a, 332b, 332c, 332e, 332f, 332g. In another embodiment, the currently-selected trend time period can be displayed by showing only the one of the trend time buttons 332a, 332b, 332c, 332d, 332e, 332f, 332g associated with the currently-selected trend time period, by providing text identifying the currently-selected trend time window, and/or otherwise identifying the currently-selected trend time window. A reminder of the trend time buttons 332a, 332b, 332c, 332e, 332f, 332g can be configured to appear in response to selecting a preferences menu (not shown) within the trend time window 311 and/or elsewhere on the display screen 300 so as to allow changing of the currently-selected trend time window.

Instead of including a plurality of trend time periods in the form of selectable buttons, e.g., the trend time buttons 332a, 332b, 332c, 332d, 332e, 332f, 332g, from which a user can select a trend time period to be used for the displayed parameter information, the trend time window 311 can additionally or alternatively include another trend time adjustment mechanism. For example, the trend time window 311 can include a trend time adjustment mechanism in the form of a text entry field configured to allow user input of text thereto, the input text identifying the trend time window, e.g., user text entry of "1" for a trend time window of one hour, user entry of "2" for a trend time window of two hours, etc. For another example, the trend time adjustment mechanism can include a slidable bar configured to be slid along a timeline having one end define an upper limit of the trend time period and the other end define a lower limit of the trend time period. A selected position of the slidable bar along the timeline can indicate the trend time period. For another example, the trend time adjustment mechanism can include a zoom in/zoom out feature of a capacitive touchscreen. Zooming in, e.g., by a user making a zoom-in or pinch touch gesture on the touchscreen, can shorten the trend time period, and zooming out, e.g., e.g., by a user making a zoom-out or spread touch gesture on the touchscreen, can lengthen the trend time period.

The trend time period can be selectively adjustable in length, such as by selecting different ones of the buttons trend time buttons 332a, 332b, 332c, 332d, 332e, 332f, 332g. In an exemplary embodiment, the trends window 310 can be configured to have selectively adjustable start and end dates and times for the selected trend time period. Adjusting the start and end dates and times of the selected trend time period can facilitate diagnosis, assessment, and/or treatment of the patient by allowing different periods of time to be viewed and/or analyzed. The start and end dates and times can be adjusted in a variety of ways. In one embodiment, the trends window 310 can include a text entry field (not shown) configured to allow user input of start and end dates and times of the selected trend time period. In another embodiment, the trends window 310 can include a calendar feature configured to allow a user to scroll through dates and times to select specific start and end dates and times of the selected trend time period. In yet another embodiment, the trends window 310 can include a trend preferences button (not shown) configured to be activated to allow adjustment of start and end dates and times of the trend time period, such as by providing a preferences window in which start and end dates and times of the trend time period can be selected. As in the illustrated embodiment, a timeline 307 can be configured to allow selection of start and end dates and times thereof. The selection can be provided in any number of ways, such as in the illustrated embodiment where a forward button 307f and a back button 307b are provided. The forward button 307f can be configured to be activated to scroll forward in time to adjust the trend time period forward. Similarly, the back button 307b can be configured to be activated to scroll back in time to adjust the trend time period backward. One or both of the back and forward buttons 307b, 307f can be configured to initially scroll at a first speed through time and be configured to scroll at a second, faster speed if held down for a predetermined amount of time, e.g., at least two seconds, at least three seconds, etc., or otherwise activated for fast scrolling, e.g., double clicked instead of single clicked.

The graphical displays of the trends window 310 can be configured to automatically update to reflect changed start and end dates and times of the trend time period. In other words, trendlines in the graphical displays can be configured to dynamically change to reflect values between the currently selected start and end of the trend time period. The trendlines can thus be time aligned with the start and end dates and times of the time period. Thus, in the illustrated embodiment, activation of the back button 307b can cause the trendlines 348t, 352t, 374t, 376t to dynamically update and each reflect an earlier date/time, and activation of the forward button 307f can cause the trendlines 348t, 352t, 374t, 376t to dynamically update and each reflect a later date/time.

In the illustrated embodiment, the trends window 310 is configured to show information for ICP, MAP, EVD ICP, CPP, HR, PbO2, and Tb, but as mentioned above, any one or more physiological parameters can be monitored and displayed, and information for any one or more physiological parameters can be shown on the trends window 310. The information displayed for each of the physiological parameters can be based on data received by the monitoring device in any of a variety of ways, as mentioned above.

For each of the physiological parameters, the trends window 310 can be configured to show a textual display of parameter information for the trend time period and/or a graphical display of parameter information for the trend time period. The textual display and/or the graphical display for each of the physiological parameters ICP, MAP/BP and HR, EVD level, CPP, PbO2, and Tb shown on the trends window 310 can be configured to be observed by a user, e.g., viewed on the screen 300, so as to assess the patient's condition. In the illustrated embodiment, the trends window 310 includes a textual display 346 and a graphical display 348 for ICP, a textual display 350 and a graphical display 352 for MAP/BP, a textual display 354 and a graphical display 374 for EVD ICP, a textual display 376 and a graphical display 378 for CPP, a textual display 380 for pbO2, a textual display 382 for Tb, and a textual display 384 for HR. Which one or more of the physiological parameters have a textual display only, have a graphical display only, or have both a textual display and a graphical display can be user-adjusted, such as by dragging and dropping displays on the touchscreen, activating a menu button, actuating one of the textual displays in the current data window 312, etc. Graphical displays for one or more of the physiological parameters can be hidden due to one or more factors such as a desire to maximize a size of shown graphical displays, a large number of physiological parameters, space limitations on the display screen 300, etc. In the embodiment illustrated in FIG. 3, graphical displays are hidden for PbO2, Tb, and HR, which do have textual displays 380, 382, 384 on the trends window 310. In an exemplary embodiment, graphical displays can be configured to automatically hidden based on a predetermined number of graphical displays that can be shown on the trends window 310 at a time. The predetermined number of graphical displays is three in the illustrated embodiment, but any number one or greater is possible. The predetermined number of graphical displays can be a user-adjustable number, e.g., by selecting a menu button. The predetermined number of graphical displays can be based on any one or more factors, such as a screen size, screen resolution, etc.

Hidden graphical display(s) can be accessed in a variety of ways. In an exemplary embodiment, the trends window 310 can include a scroll element, e.g., a scroll button, a text selection menu, a slidable scroll bar, etc., configured to allow scrolling through the physiological parameters to allow hidden graphical displays to be viewed on the trends window 310. The scroll element in the illustrated embodiment includes a touch-activated scroll button 386 and at least one arrow included therein and/or adjacent thereto that indicates a direction available for scrolling. In the illustrated embodiment, an arrow 386a included in the button 386 and another arrow 386b adjacent the button 386 point down because the three hidden parameters are ordered below the three non-hidden parameters. As discussed further below, order of the parameters can be adjusted. The scroll button 386 can include down arrow(s) only, up arrow(s) only, or both up and down arrows based on where hidden parameters are located in the order of parameters. If all parameters are shown on the trends window 310, e.g., if no parameters' graphical displays are hidden, the trends window 310 can lack a scroll element.

In some instances, data may not be received for a certain physiological parameter, such as if a sensing device for the certain physiological parameter is not attached to the patient or if a sensing device for the certain physiological parameter attached to a patient has not been electronically connected to a processor that processes data to be displayed on the display screen 300. If data is not received for one or more physiological parameters, textual and graphical display(s) for those one or more physiological parameters can be absent from the display screen 300. Both the textual display(s) and the graphical display(s) for those one or more physiological parameters can be present on the current data window 312 and/or the currently selected window, which is the trends window 310 in FIG. 3, but lack any numerical or graphed data, or one of the graphical display(s) and textual display(s) for those one or more physiological parameters can be absent from the current data window 312 and/or the trends window 310 while the other of the graphical display(s) and textual display(s) for those one or more physiological parameters can be present on the current data window 312 and/or the trends window 310. By having at least one of the textual display(s) and the graphical display(s) for those one or more parameters present on the current data window 312 and/or the trends window 310, it can be easier for a user observing the current data window 312 and/or the trends window 310 to determine, based on a lack of data in those graphical and/or textual display(s), that those one or more parameters are not being monitored or that the sensing device(s) for those one or more parameters are not properly configured. The present textual and/or graphical display(s) for those one or more parameters can each include at least one data absence indicator, e.g., a textual message, a warning symbol, etc., indicating that data is not being received.

Figure 5:
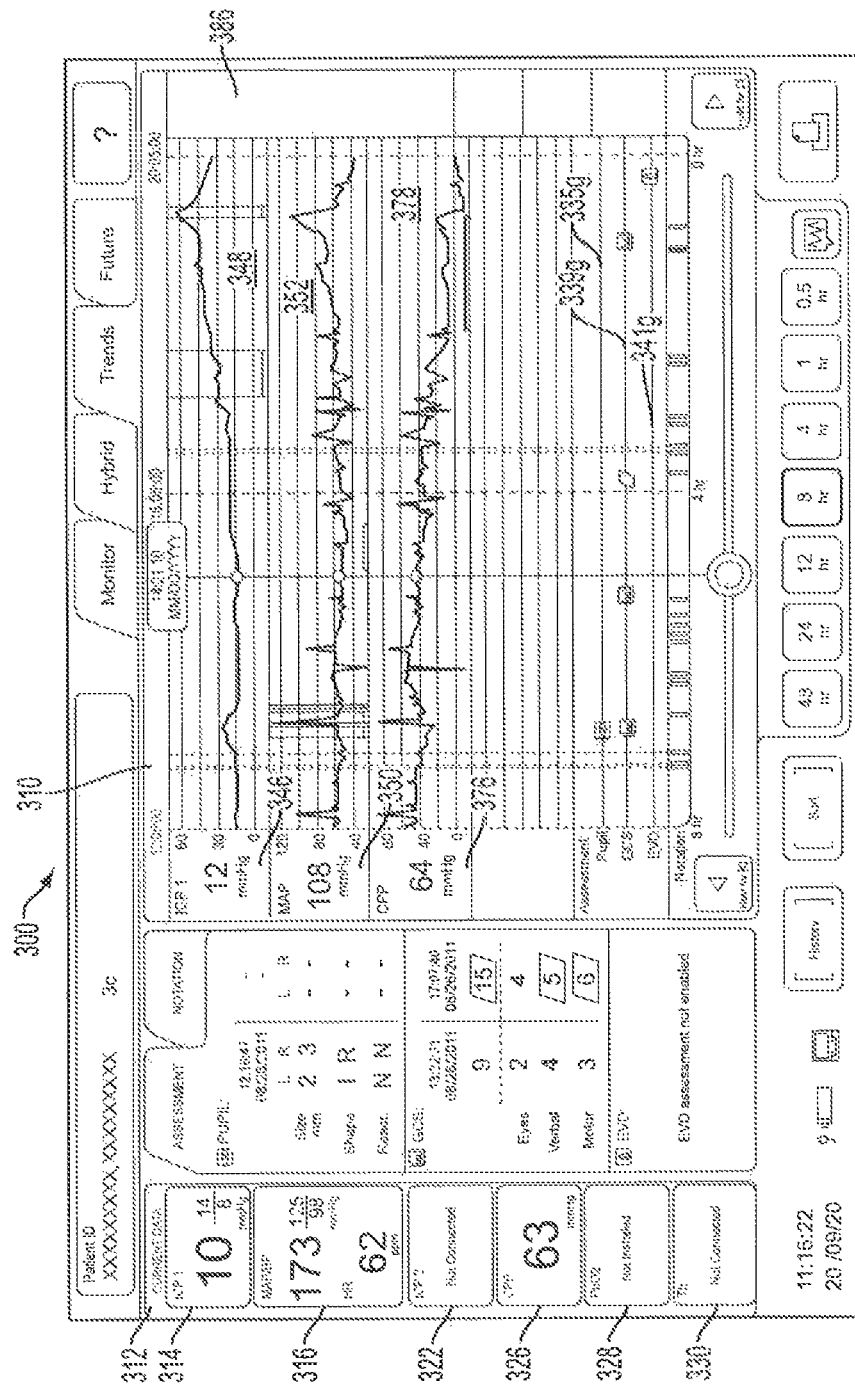
FIG. 5 shows the trends window of FIG. 3 including trends information and current data information for a subset of the physiological parameters.

FIG. 5 shows an example of the display screen 300 in which data is being received for a plurality of physiological parameters, e.g., ICP, MAP/BP, and CPP, and is not being received for another plurality of physiological parameters, e.g., EVD ICP, PbO2, and Tb. The display screen 300 in this illustrated embodiment thus lacks textual and graphical displays for EVD ICP, PbO2, and Tb in the trends window 310 and lacks any numerical data in the textual displays 322, 328, 330 in the current data window 312 for EVD ICP, PbO2, and Tb. In the illustrated embodiment, the textual displays 322, 328, 330 in the current data window 312 for EVD ICP, PbO2, and Tb each include a data absence indicator in the form of a textual message, "Not connected" in the EVD ICP and Tb displays 322, 330 and "Not installed" in the PbO2 display 328. FIG. 5 also shows an example of a scroll element being unnecessary because all graphical displays 348, 352, 378 for "active" parameters are shown on the trends window 310. The scroll button 386 is thus grayed out in FIG. 5, thereby indicating that the scroll button 386 cannot be actuated even if touched on the touchscreen.

Figure 6:
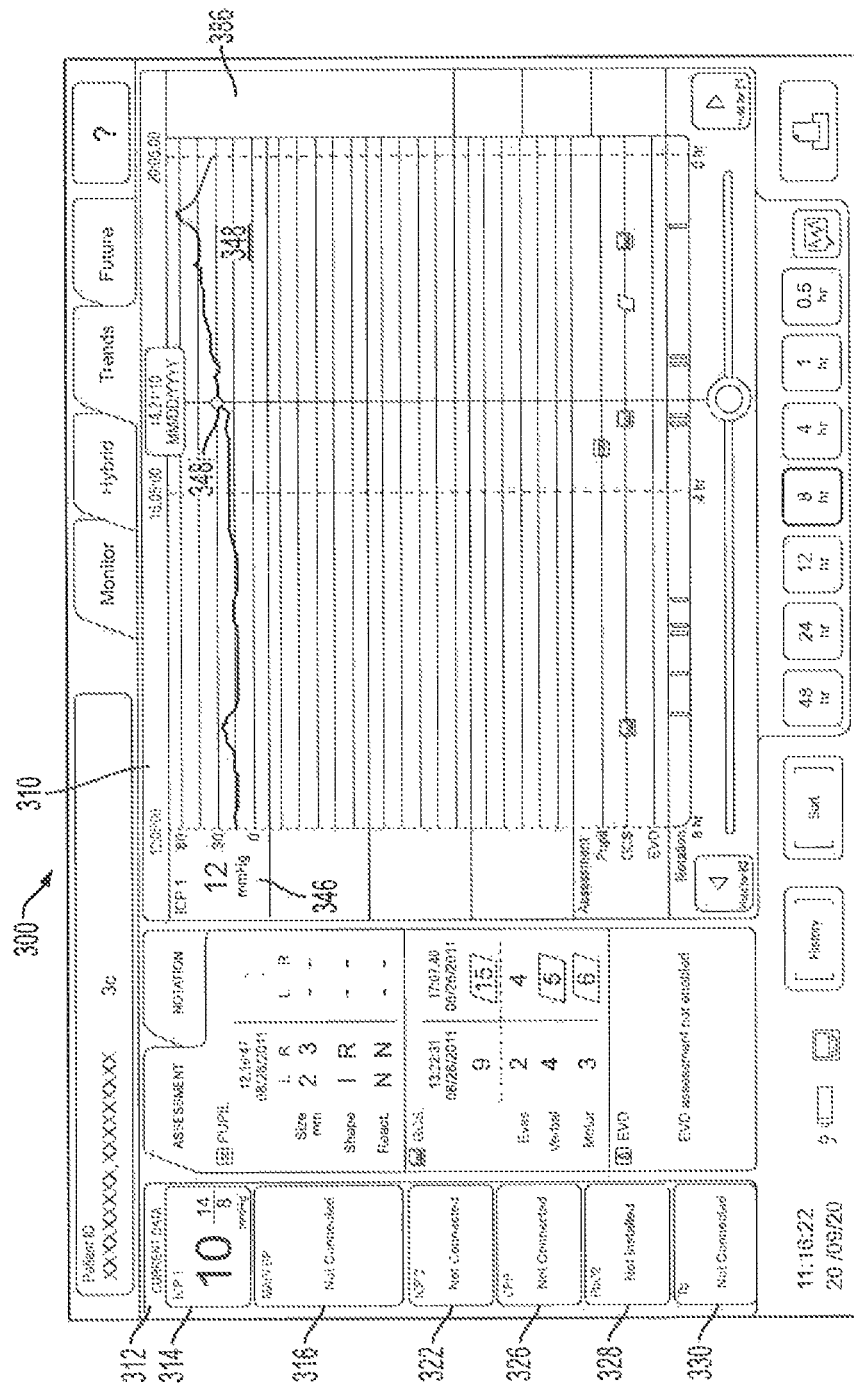
FIG. 6 shows the trends window of FIG. 3 including trends information and current data information for another subset of the physiological parameters.

FIG. 6 shows an example of the display screen 300 in which data is being received for a single physiological parameter, e.g., ICP, and is not being received for a plurality of physiological parameters, e.g., MAP/BP and HR, CPP, EVD ICP, PbO2, and Tb. The display screen 300 in this illustrated embodiment thus lacks textual and graphical displays for MAP/BP and HR, CPP, EVD ICP, PbO2, and Tb in the trends window 310 and lacks any numerical data in the textual displays 318, 322, 326, 328, 330 in the current data window 312 for MAP/BP and HR, CPP, EVD ICP, PbO2, and Tb. In the illustrated embodiment, the textual displays 318, 322, 326, 328, 330 in the current data window 312 for MAP/BP and HR, CPP, EVD ICP, PbO2, and Tb each include a data absence indicator in the form of a textual message, "Not connected" in the MAP/BP and HR, EVD ICP, CPP, and Tb displays 318, 322, 326, 330 and "Not installed" in the PbO2 display 328. FIG. 6 also shows an example of a scroll element being unnecessary because all graphical displays 348 for "active" parameters are shown on the trends window 310. The scroll button 386 is thus grayed out in FIG. 6, thereby indicating that the scroll button 386 cannot be actuated even if touched on the touchscreen.

Figure 7:
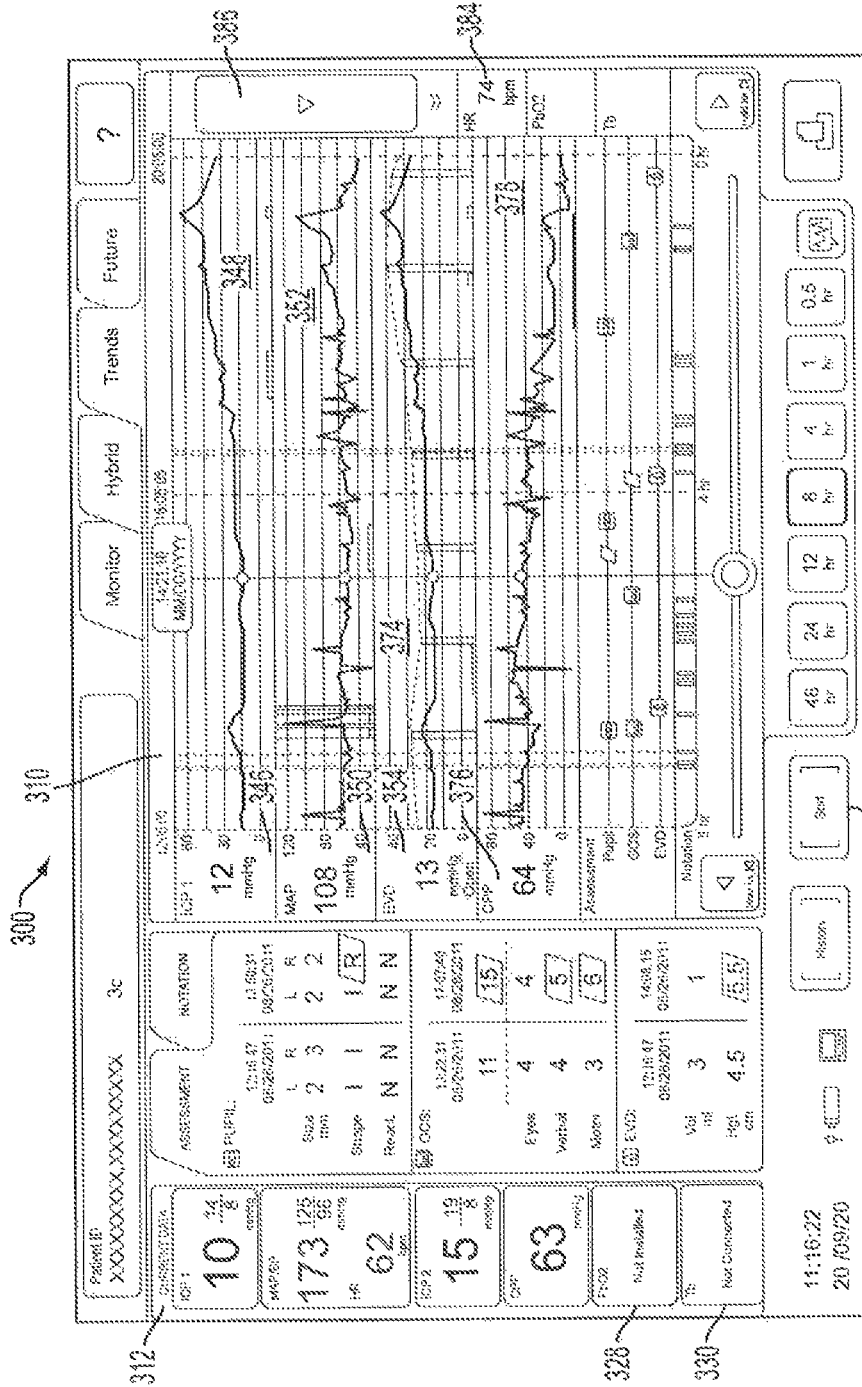
FIG. 7 shows the trends window of FIG. 3 including trends information and current data information for another subset of the physiological parameters.

FIG. 7 shows an example of the display screen 300 in which data is being received for a plurality of physiological parameters, e.g., ICP, MAP/BP and HR, EVD ICP, and CPP, and is not being received for a plurality of physiological parameters, e.g., PbO2 and Tb. The display screen 300 in this illustrated embodiment thus lacks textual and graphical displays for PbO2 and Tb in the trends window 310 and lacks any numerical data in the textual displays 328, 330 in the current data window 312 for PbO2 and Tb. In the illustrated embodiment, the textual display 328, 330 in the current data window 312 for Tb includes a data absence indicator in the form of a textual message, "Not connected" in the Tb display 330 and "Not installed" in the PbO2 display 328. FIG. 7 also shows an example of the scroll button 386 being actuatable to scroll down for at least one additional graphical trends display, e.g., a graphical display for HR.

Figure 8:
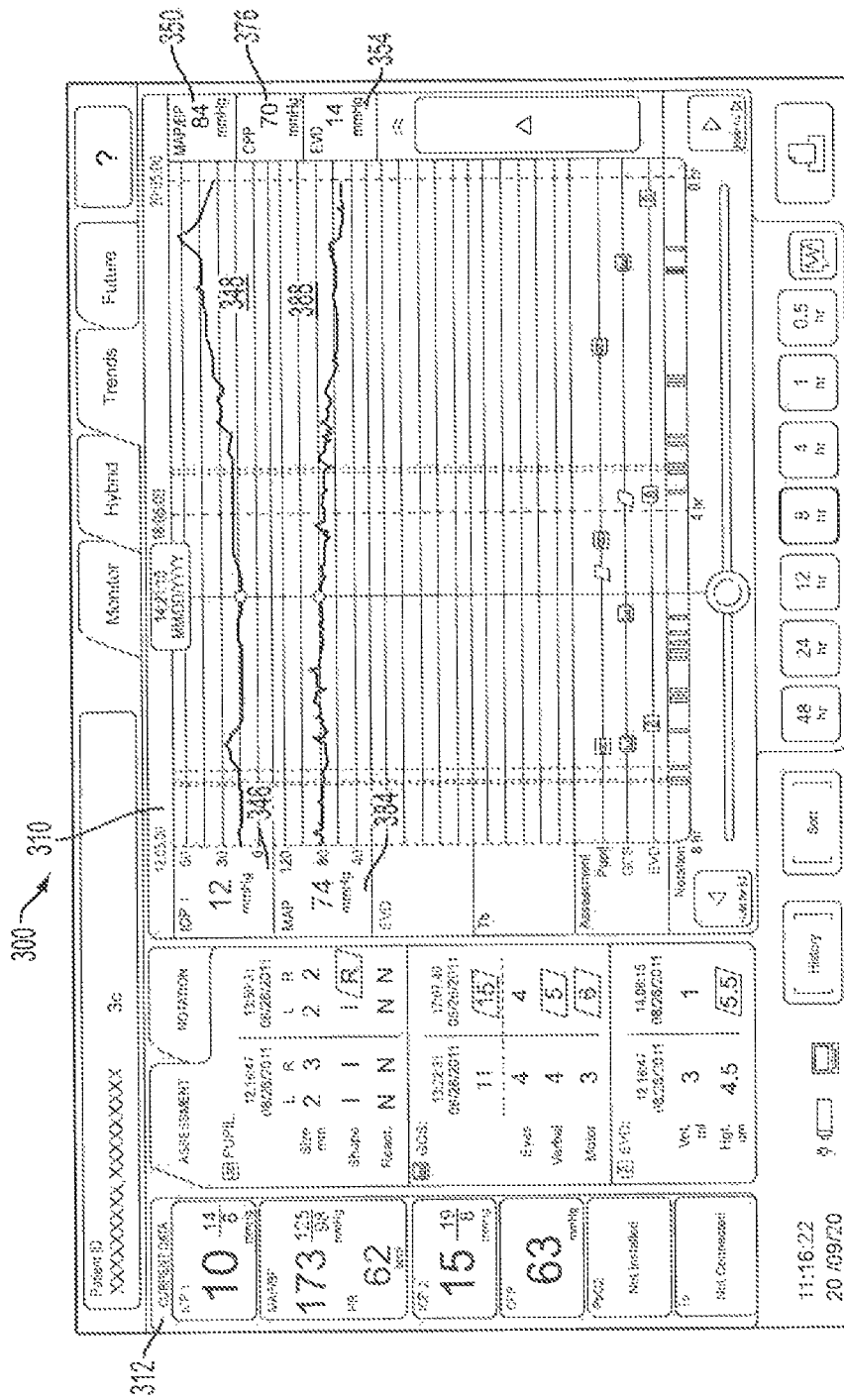
FIG. 8 shows the trends window of FIG. 3 including trends information and current data information for yet another subset of the physiological parameters.

FIG. 8 shows yet another example of the display screen 300 in which data is being received for a plurality of physiological parameters, e.g., ICP, MAP/BP and HR, EVD ICP, and CPP, and is not being received for a plurality of physiological parameters, e.g., PbO2 and Tb. The display screen 300 in this illustrated embodiment thus lacks textual and graphical displays for PbO2 and Tb in the trends window 310 and lacks any numerical data in the textual displays 328, 330 in the current data window 312 for PbO2 and Tb. In the illustrated embodiment, the textual display 328, 330 in the current data window 312 for Tb includes a data absence indicator in the form of a textual message, "Not connected" in the Tb display 330 and "Not installed" in the PbO2 display 328. FIG. 8 also shows an example of the scroll button 386 being actuatable to scroll up for at least one additional graphical trends display, e.g., a graphical display for MAP/BP, CPP, and EVD ICP, that are currently hidden while graphical displays 348, 388 are shown for ICP and HR.

While FIG. 8 has available graphical displays 348, 352, 374, 378, 388 for the same parameters ICP, MAP/BP, EVD ICP, CPP, and HR as in FIG. 7, the parameters are in different orders in FIGS. 7 and 8 such that different graphical displays are shown in FIGS. 7 and 8. More particularly, the parameters are ordered from top to bottom in FIG. 7 as ICP, MAP/BP, EVD ICP, CPP, and HR, while the parameters are ordered from top to bottom in FIG. 8 as MAP/BP, CPP, EVD ICP, ICP, and HR. As mentioned above, ordering of parameters can be adjusted, such as to facilitate comparison of two or more parameters by arranging graphical displays for those two or more parameters to be adjacent to one another on the trends window 310. Selection of the sort button 358 can allow for reordering of parameters, as mentioned above. Selecting the sort button 358 can, for example, provide on the screen 300 a list of available parameters in their current order. One or more parameters can be dragged and dropped to new places within the list so as to reorder the parameters.

One or more parameters can be frozen at a top of the parameter order, which can facilitate comparison of the frozen parameter(s) with each of the other parameters as the other parameters scroll on/off the trends window 310. Selecting the sort button 358 can allow the frozen parameter(s) to be chosen. Similarly, any frozen parameter(s) can be unfrozen, such as by selecting the sort button 358.

Figure 9:
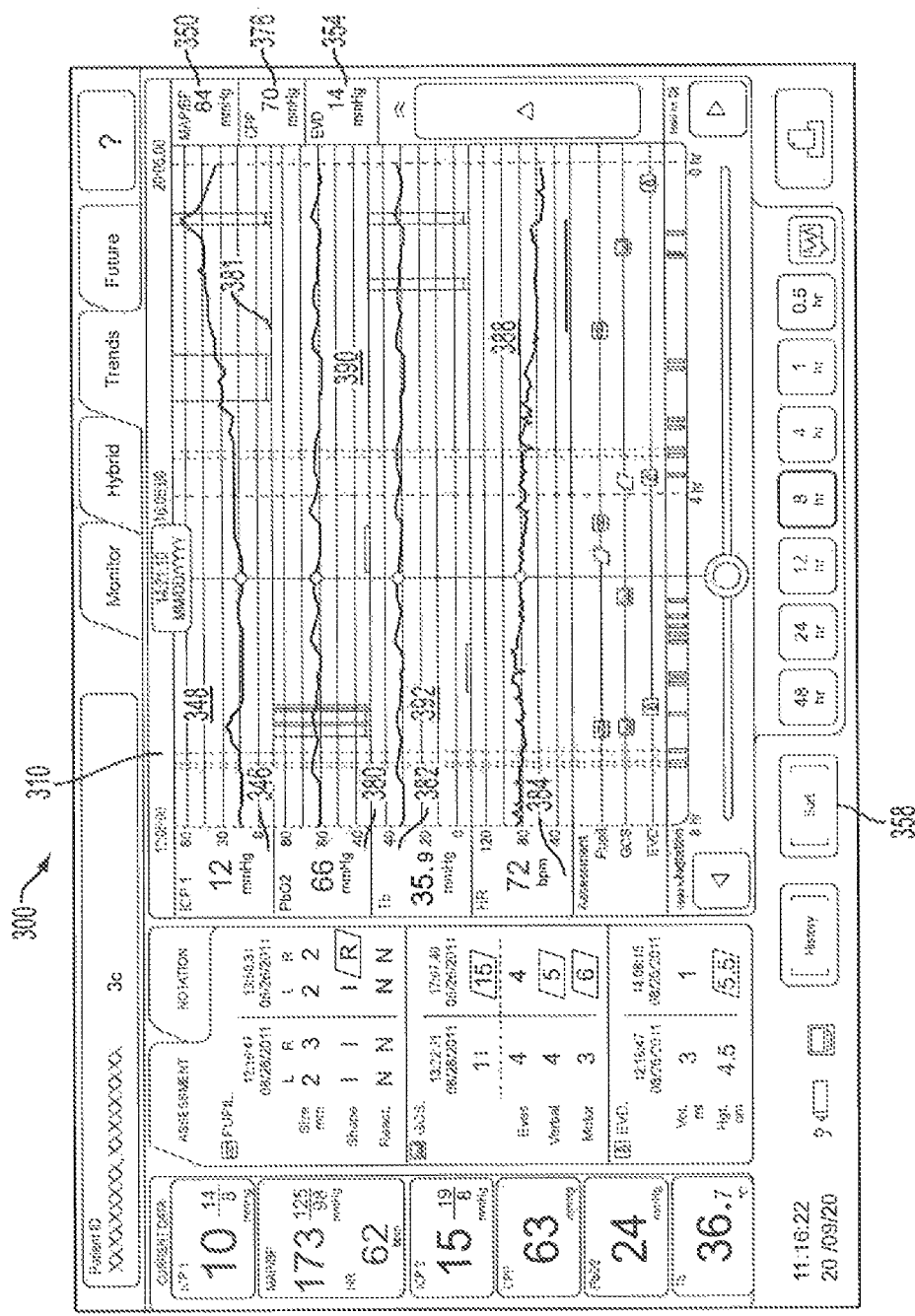
FIG. 9 shows the trends window of FIG. 3 including trends information and current data information for another subset of the physiological parameters.

FIG. 9 illustrates an example of the trends window 310 including at least one frozen parameter, which includes ICP in this illustrated example. The frozen parameter can identified as being frozen on the display screen 300 in any one or more ways, such as by being indicated with a text identifier, e.g., "Frozen," in the frozen parameter's textual display and/or graphical display, with background shading of the frozen parameter's textual display and/or graphical display (as in the illustrated embodiment in which the ICP textual and graphical displays 346, 348 have a different background color (a lighter shade of grey in the illustrated embodiment) than the other textual displays 380, 382, 384 and graphical displays 390, 392, 388 for Pb02, Tb, and HR, by showing a divider line 381 between frozen display(s) and non-frozen display(s), etc. FIG. 9 also shows an example of the scroll button 386 being actuatable to scroll up for at least one additional graphical trends display, e.g., a graphical display for MAP/BP, CPP, and EVD ICP, that are currently hidden while graphical displays 348, 390, 392, 388 are shown for ICP, Pb02, Tb and HR.

Referring again to FIG. 3, the textual display for each physiological parameter can include numerical data regarding the physiological parameter for the trend time period, and the graphical display for each physiological parameter can include a graphical illustration of the numerical data for the trend time period. For ease of discussion, the textual display 314 and the graphical display 348 for ICP are discussed below as representative examples of textual and graphical displays for a physiological parameter shown on the trends window 310. Textual and graphical displays for other physiological parameters shown on the trends window 310 can be similarly configured.

The graphical display 348 can represent ICP graphically with a trendline 348t, in the form of a waveform or graph line, plotted over the trend time period, e.g., the trend time selected via one of the selectable trend time buttons 332a, 332b, 332c, 332d, 332e, 332f, 332g. However, virtually any graphical representation can be used, such as a graph line, a bar graph, a plot of discrete data points, and/or other pictorial display. The graphical display 348 in the illustrated embodiment plots via the trendline 348t ICP values gathered and/or calculated during the trend time period, which as mentioned above is eight hours in the illustrated embodiment. Similarly, the trends window 310 shows trendlines 352t, 374t, 376t in the other graphical displays 352, 374, 376 spanning eight hours. The graphical display 348 can show (e.g., via a graph line and/or other pictorial display) values of another statistic based on ICP, e.g., a mean value of the physiological parameter calculated over a sample period, e.g., every two to three seconds, a median value, a normalized value, a systolic value, a diastolic value, wave amplitude, etc. In an exemplary embodiment, if the trends window 310 shows information for a plurality of physiological parameters, as in the illustrated embodiment, the same statistic(s) are shown on the trends window's graphical displays for each of the parameters, thereby facilitating quick identification and understanding of the displayed information.

Figure 10:
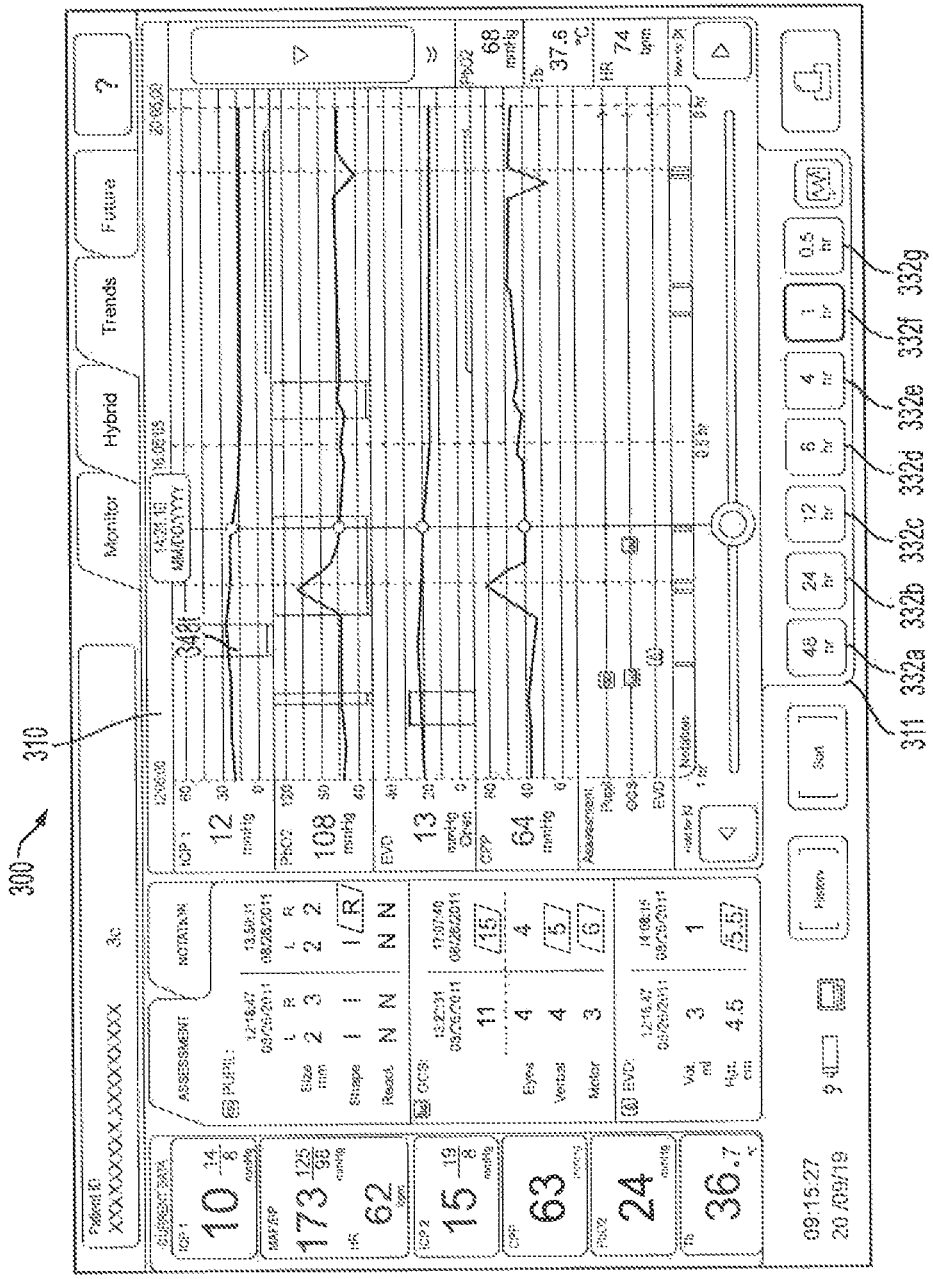
FIG. 10 shows the trends window of FIG. 3 for another trends period of time.
Figure 11:
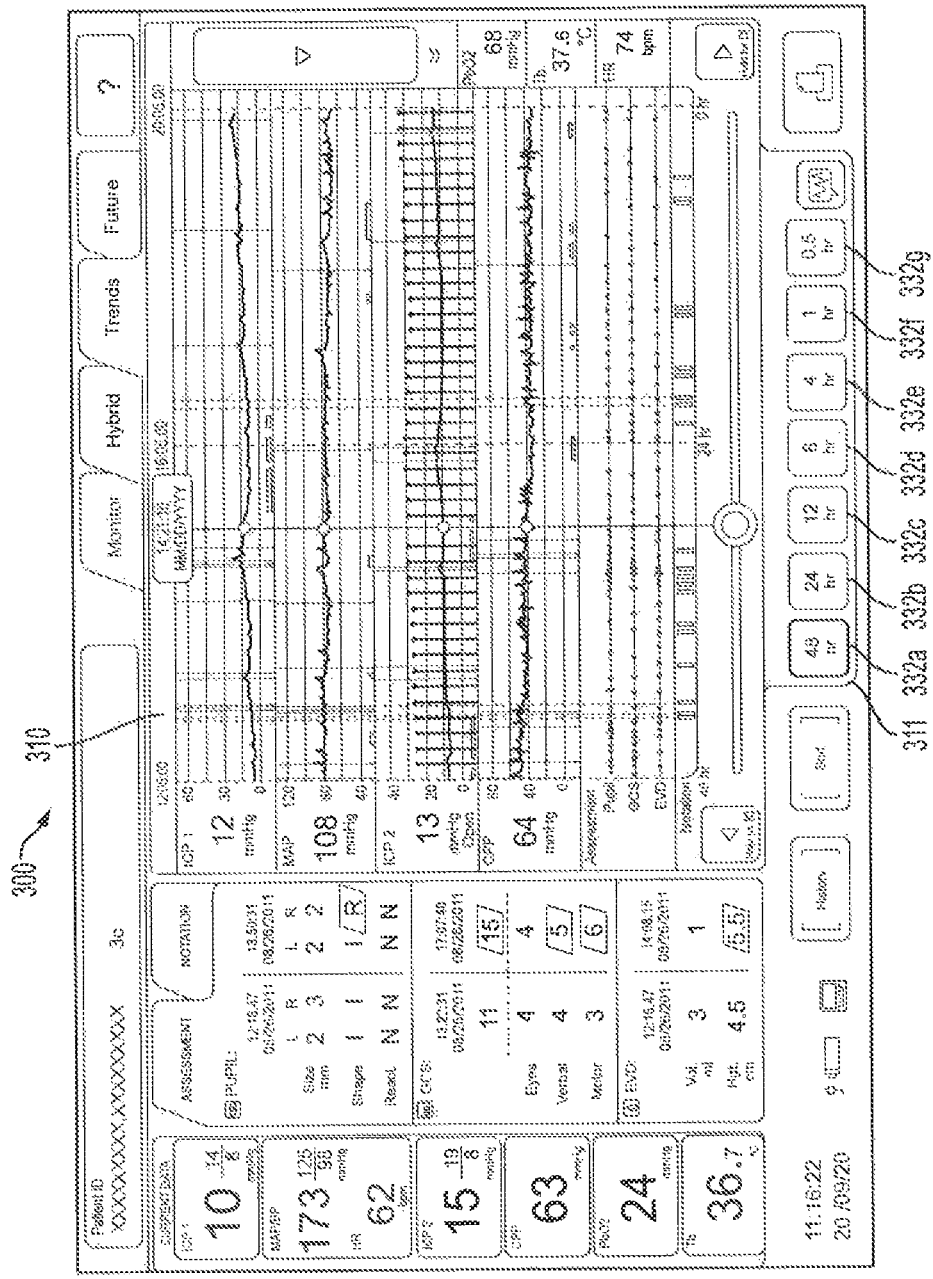
FIG. 11 shows the trends window of FIG. 3 for yet another trends period of time.

FIGS. 10 and 11 illustrate embodiments in which the ICP trendline 348t is shown over trend time periods other than eight hours. FIG. 10 illustrates an embodiment in which a one hour trend time period is selected, e.g., by selection of the "1 hr" trend time button 332f, such that the trendline 348t shows the current value (e.g., average ICP) over a one hour time period and similarly shows the trendlines 352t, 374t, 376t in the other graphical displays 352, 374, 376 spanning one hour. FIG. 11 illustrates an embodiment in which a forty-eight hour trend time period is selected, e.g., by selection of the "48 hr" trend time button 332a, such that the trendline 348t shows the current value (e.g., average ICP) over a forty-eight hour time period and similarly shows the trendlines 352t, 374t, 376t in the other graphical displays 352, 374, 376 spanning forty-eight hours.

Referring again to FIG. 3, the textual display 346 can represent ICP textually and/or pictorially. In the illustrated embodiment, the textual display 346 includes information related to an average of ICP values gathered and/or calculated during the trend time period including a current average (e.g., the current average intracranial pressure) over the trend time period. Although a current value related to ICP is an average of gathered values in the illustrated embodiment, as mentioned above, other current values can be shown instead of or in addition to the average of gathered values, e.g., an average of a calculated index (e.g., an average of peak gathered values, an average of a rate of change of the gathered values, etc.), a median of gathered values, a rate of change of gathered values, a correlation (e.g., PRx, RAP, autocorrelation, an average of autocorrelation, etc.), a maximum value among the gathered values, a minimum value among the gathered values, a root mean square (RMS), peak-to-peak values, etc.

The current value can be shown textually and/or graphically. In the illustrated embodiment, the current average is shown textually with a numerical value 347. The average ICP value in the illustrated embodiment is 12 mmHg. As will be appreciated by a person skilled in the art, the numerical value 337 shown on the trends window 310 can be an exact average value or can be a rounded value, e.g., rounded to a nearest whole number (as in the illustrated embodiment), rounded to one decimal place, rounded to two decimal places, etc. The numerical value 347 shown for ICP in the textual display 346 of the trends window 310 can be different than the numerical value 334 in the current data window 312, as in the illustrated embodiment, since the numerical value 347 shown for ICP in the textual display 346 of the trends window 310 is based on the trend time period, whereas the numerical value 334 in the current data window 312 is based on the current time period. In an exemplary embodiment, the numerical values 334, 347 are of a same type of current value, e.g., both averages of gathered values, so as to facilitate comparison of the physiological parameter over different time periods.

The textual displays and/or the graphical displays for any one or more of the physiological parameters shown in the trends window 310 and/or in the current data window 312 can include other information regarding their respective physiological parameters. For example, still using ICP as a representative example, the textual display 314 in the current data window 312 can include a sensing device position indicator (not shown) that indicates a position (e.g., (L/R parenchyma, L/R ventricle, or lumbar) of a sensing device (not shown) sensing ICP from the patient so as to gather ICP values therefrom. The position can be entered manually. For another example, the textual display 354 and/or the graphical display 374 for EVD ICP can indicate textually and/or graphically whether or not the EVD having the EVD ICP is an open state or a closed state. As will be appreciated by a person skilled in the art, a default state of an EVD is typically the closed state. The EVD being in the closed state can be indicated by, e.g., not providing any particular textual or graphical indication regarding the EVD's open or closed state. FIG. 3 illustrates an embodiment in which the EVD is indicated as being in the open state, e.g., that the EVD opened to relieve excess cerebral spinal fluid (CSF) in the brain. The open state is indicated in the FIG. 3 embodiment with a textual EVD state indicator 355 ("Open") in the EVD textual display 354 and a graphical EVD state indicator in the form of background shading in the EVD graphical display 374. The textual EVD state indicator 355 can have another configuration (e.g., "open state," "EVD open," "closed," "EVD closed," etc.), and the graphical EVD state indicator can also have other configurations (e.g., a schematic illustration of an open EVD device, etc.)

To facilitate assessment of the patient's condition, an alarm, e.g., an audible sound, a flashing window, an illuminated light, a color change on the display screen 300, a page to an attending physician, etc., can be provided if any of the monitored physiological parameters fall outside their associated normal range. The alarm can be provided in a variety of ways. In an exemplary embodiment, when a current value of one of the physiological parameters, e.g., ICP, MAP/BP, HR, EVD level, CPP, PbO2, and Tb, shown on the trends window 310 (e.g., in any of the current data window 312, the textual displays 346, 350, 354, 376, 380, 382, 384, and the graphical displays 348, 352, 374, 378) falls outside its associated predetermined normal range, the alarm can be triggered. In other words, when a current value of one of the physiological parameters increases to be above the predetermined upper normal limit for that physiological parameter or decreases to be below the predetermined lower normal limit for that physiological parameter, the alarm can be triggered. In other words, when the physiological parameter's average falls outside the normal range as determined by the device's processor, the processor can cause the device's alarm to activate. An alarm may exist for a parameter in only one of the current data window 312 and the parameter's associated textual and graphical displays because of the differing time periods used in the current data window 312 and the parameter's associated textual and graphical displays. Various embodiments of providing alarms for physiological parameters are discussed in further detail in U.S. application Ser. No. 13/803,667 entitled "Methods, Systems, And Devices For Monitoring And Displaying Medical Parameters For A Patient" filed on Mar. 14, 2013.

In the illustrated embodiment of FIG. 3, the ICP, MAP/BP, HR, ICP 2, CPP, PbO2, and Tb physiological parameters are within their respective normal ranges such that alarms are not shown for any of MAP/BP, HR, ICP 2, CPP, PbO2, and Tb. Any one or more of the parameters on the screen 300 can, in any combination thereof, have alarms therefor.

When an alarm is triggered, the alarm can persist, e.g., a sound can continue sounding, the textual display's background color can remain its changed color, the textual display's background color can flash, a warning light attached to the display can continue flashing, etc., until the alarm is acknowledged by a user and/or until the out-of-normal range parameter's average falls back within the normal range. The alarm can be acknowledged in a variety of ways, such as by activating an alarm silence button (not shown). In an exemplary embodiment, the alarm silence button can appear only when an alarm is triggered.

When the alarm is acknowledged, the display screen 300 can continue to indicate that the out-of-normal-range parameter is outside the normal range until the parameter returns to within the normal range. In this way, the display screen 300 can indicate that the alarm condition has been observed by at least one medical practitioner, e.g., nurse, doctor, etc. Thus, any subsequent observer of the display screen 300 while the alarm condition persists can determine from the display screen 300 that the alarm has been previously observed and is likely being tended to as needed. The display screen 300 can display an acknowledged alarm in a variety of ways. In an exemplary embodiment, the acknowledged alarm for an out-of-normal-range physiological parameter can include at least a color change on the display screen 300 for the out-of-normal-range physiological parameter. The portion(s) of the screen 300 associated with the out-of-range parameter that changed to indicate the alarm can change again similar to that discussed above regarding the change to indicate the alarm, e.g., change from one color to another color. Various embodiments of acknowledging alarms for physiological parameters are discussed in further detail in U.S. application Ser. No. 13/803,667 entitled "Methods, Systems, And Devices For Monitoring And Displaying Medical Parameters For A Patient" filed on Mar. 14, 2013.

Figure 12:
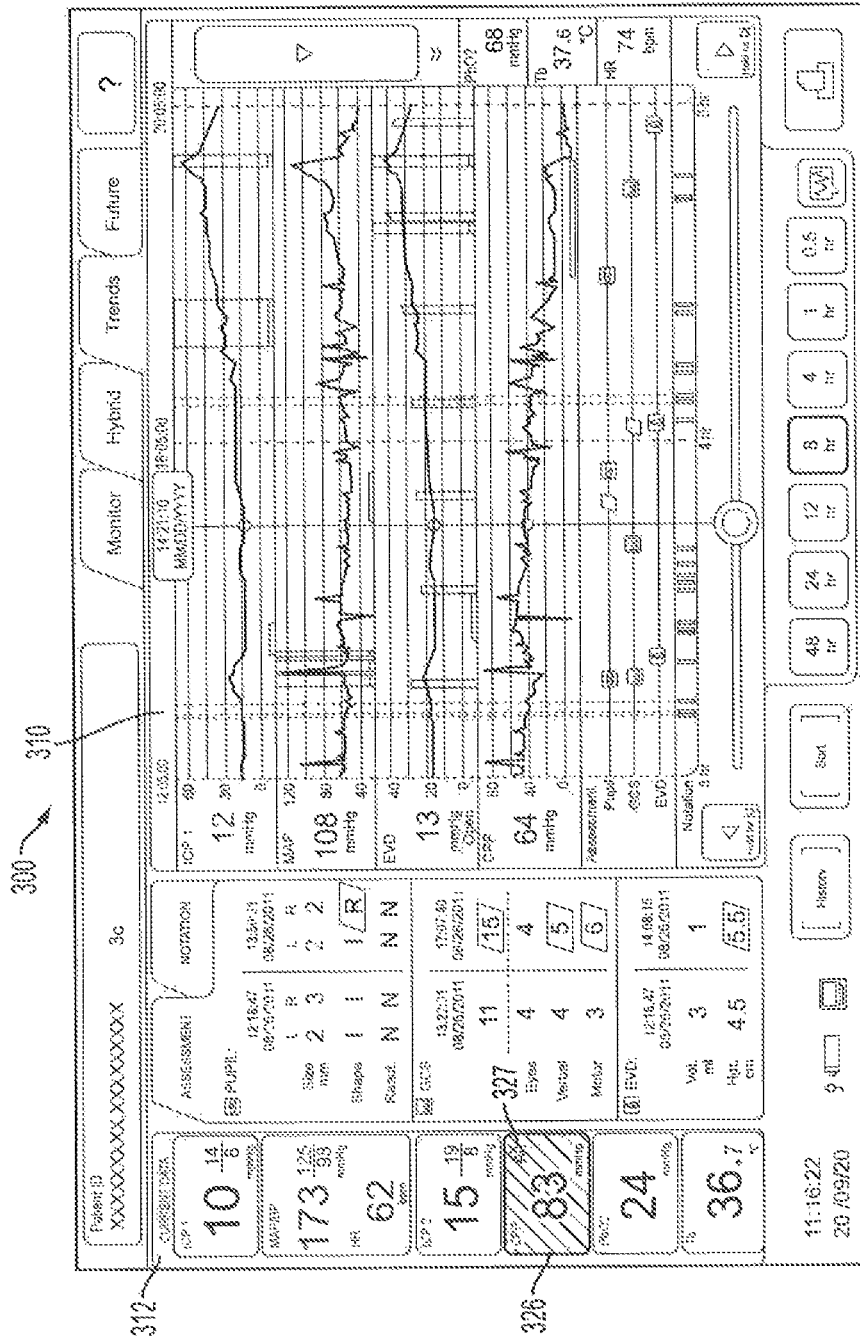
FIG. 12 shows the trends window of FIG. 3 including an acknowledged alarm for one of the physiological parameters.

FIG. 12 shows an embodiment of the display screen 300 after acknowledgement of an alarm regarding out-of-normal-range CPP. In response to the alarm being acknowledged, e.g., in response to activation of an alarm silence button, an acknowledgement was triggered, thereby changing a background color for the CPP textual display 326 in the current data window 312 from one color, e.g., red, to another color, e.g., white, in FIG. 12. An alarm symbol 327 can remain present on the display screen 300 even after the alarm has been acknowledged, as shown in FIG. 12.

The trends window 310 can be configured to indicate whether or not a physiological parameter was in an alarm state during the trend time period shown in the trends window 310. In other words, the trends window 310 can be configured to indicate when an alarm was triggered for a physiological parameter, e.g., when the physiological parameter was outside its associated normal range, and how long the alarm persisted, e.g., when the physiological parameter returned to within its associated normal range. The trends window 310 can thus be configured to provide historical alarm data regarding each of the physiological parameters, thereby facilitating patient care and/or saving time by providing more information regarding the patient in one place. In an exemplary embodiment, the trends window 310 can be configured to indicate specific dates and times during the trend time period shown in the trends window 310 in which any of the physiological parameters were outside their respective normal ranges.

The trends window 310 can be configured to indicate historical alarm information for a physiological parameter in a variety of ways. In an exemplary embodiment, the trends window 310 can be configured to include an alarm marker within the graphical display of the physiological parameter which had one or more alarm states during the trend time period shown in the trends window 310. If multiple alarm states existed for the parameter, the parameter's graphical display can include an alarm marker for each of the alarm states, thereby providing a more complete picture of the parameter's history.

The alarm marker can be positioned within the graphical display adjacent the dates and times corresponding to the alarm state, e.g., adjacent the trendline within the graphical display at the corresponding date and time. Being positioned adjacent the dates and times corresponding to the alarm state can facilitate comparison of alarm states for different physiological parameters because the alignment/misalignment of the alarm markers can be easily visually compared as being at same or different dates and times.

The alarm marker can have a variety of configurations, e.g., a highly color-contrasted portion of the trends window 310, a symbol shown on the trends window 310, shading within the trends window 310, a bolded portion of the trendline, a line adjacent the trendline, etc. A color of the alarm marker can correspond to a color of the alarm provided on the display screen, which in the illustrated embodiment is a red color, but any color(s) can be used. In the illustrated embodiment of FIG. 3, the alarm marker includes a line extending timewise within a graphical display and a shaded portion within the graphical display in a portion thereof corresponding to the line. By way of example, FIG. 3 shows alarm marker shading 348s and an alarm marker line 3481 at two different times in the ICP graphical display 348, alarm marker shading 352s and an alarm marker line 3521 at three different times in the MAP graphical display 352, and alarm marker shading 374s and an alarm marker line 3741 at two different times in the EVD graphical display 374. The alarm markers in the illustrated embodiment can allow dates and times of alarms for different parameters to be easily compared, as mentioned above, such as to determine that each of ICP and ICP2 (EVD) had concurrent alarm states at about 19:10:00, as shown in FIG. 3. No alarm marker is shown in the CPP graphical display 378, thereby indicating that CPP was not in an alarm state in the trend time period shown on the trends screen 310.

Similar to that discussed above regarding the alarm for the normal range, to facilitate assessment of the patient's condition, a goal alarm can be provided if any of the physiological parameters are outside their associated goal range. In an exemplary embodiment, the goal alarm can be provided for a physiological parameter when the physiological parameter is outside its associated goal range, which can be nested within the normal range, and is within its associated normal range. The goal alarm can indicate to medical personnel, e.g., an attending nurse, a doctor, etc., that the patient may need assessment and/or treatment because the physiological parameter associated with the goal alarm is not in an optimal range and therefore may be heading outside its normal range. In other words, the patient's condition may be deteriorating but can be assessed and/or the patient can be treated prior to the patient being in a more dire condition. The goal alarm can thus function in a preventative way. The goal alarm can be provided in a variety of ways.

In an exemplary embodiment, when an average of one of the physiological parameters, e.g., ICP, MAP/BP, HR, EVD level, CPP, PbO2, and Tb, is within its associated predetermined goal range, and hence is also within its associated normal range, a goal indicator can be shown on the display screen 300. In other words, when a current value of one of the physiological parameters is within its associated goal range, e.g., below its associated predetermined upper goal limit and above its associated predetermined lower goal limit, the goal indicator can be triggered to be displayed on the screen 300 for that physiological parameter. The device's processor can be configured to determine whether the physiological parameters' current values are within their respective the goal ranges and can be configured to cause the goal indicator to be shown on the screen 300. The statuses of the physiological parameters shown on the display screen 300 can thus be quickly assessed by checking the display screen 300, e.g., by a user looking at the display screen, to determine if a goal indicator is present on the screen 300 for each of the physiological parameters. The goal alarm for a physiological parameter can, in an exemplary embodiment, include absence of the goal indicator from the screen 300 for that physiological parameter. Various embodiments of providing goal alarms and goal indicators for physiological parameters are discussed in further detail in U.S. application Ser. No. 13/803,667 entitled "Methods, Systems, And Devices For Monitoring And Displaying Medical Parameters For A Patient" filed on Mar. 14, 2013.

The trends window 310 can be configured to indicate whether or not a physiological parameter was within its goal range during the trend time period shown in the trends window 310. In other words, the trends window 310 can be configured to indicate when a goal alarm was triggered for a physiological parameter, e.g., when the physiological parameter was outside its associated goal range, and how long the goal alarm persisted, e.g., when the physiological parameter returned to within its associated goal range. The trends window 310 can thus be configured to provide historical goal alarm data regarding each of the physiological parameters, thereby facilitating patient care and/or saving time by providing more information regarding the patient in one place. In an exemplary embodiment, the trends window 310 can be configured to indicate specific dates and times during the trend time period shown in the trends window 310 in which any of the physiological parameters were within their respective goal ranges.

The trends window 310 can be configured to indicate historical goal alarm information for a physiological parameter in a variety of ways. In an exemplary embodiment, the trends window 310 can be configured to include a goal marker within the graphical display of the physiological parameter which was within its associated goal range during the trend time period shown in the trends window 310. If the parameter was within its associated goal range at different dates/times, the parameter's graphical display can include a goal marker for each of the dates/times, thereby providing a more complete picture of the parameter's history.

The goal marker can be positioned within the graphical display adjacent the dates and times corresponding to the date/time the parameter was within its associated goal range, e.g., adjacent the trendline within the graphical display at the corresponding date and time. Being positioned adjacent the dates and times corresponding to the goal state can facilitate comparison of goal states for different physiological parameters because the alignment/misalignment of the goal markers can be easily visually compared as being at same or different dates and times.

The goal marker can have a variety of configurations similar to that discussed above regarding the alarm marker and can include, e.g., a highly color-contrasted portion of the trends window 310, a symbol shown on the trends window 310, shading within the trends window 310, a bolded portion of the trendline, a line adjacent the trendline, etc. A color of the goal marker can correspond to a color of the alarm provided on the display screen, which in the illustrated embodiment is a bright green color, but any color(s) can be used. In the illustrated embodiment of FIG. 3, the goal marker includes a line extending timewise within a graphical display. By way of example, FIG. 3 shows a goal marker line 352g at one time in the MAP graphical display 352, a goal alarm marker line 374g at one time in the EVD graphical display 374, and a goal marker line 378g at one time in the CPP graphical display 378. The goal markers in the illustrated embodiment can allow dates and times of alarms for different parameters to be easily compared, as mentioned above, such as to determine that none of ICP, MAP, EVD, and CPP in any combination had any overlapping time(s) of being within their associated goal ranges. No goal marker is shown in the ICP graphical display 348, thereby indicating that ICP was not within its associated goal range in the trend time period shown on the trends screen 310.

The trends window can be configured to allow user selection of a date and time within the currently-selected trend time period. The trend time period spans over multiple times but may not span over more than one date depending on a length of the trend time period, a start date and time for the trend time period, and an end date and time for the trend time period. Data corresponding to the user-selected date and time can be displayed on the trends window 310, thereby facilitating analysis of the patient's condition at a specific point in time. Different points in time can be compared against one another, which can facilitate diagnosis, assessment, and/or treatment of the patient and/or can facilitate detection of patterns using data from a plurality of patients.

The date and time within the currently-selected trend time period can be selected in a variety of ways. In one embodiment, the trends window 310 can include a text entry field (not shown) configured to allow user input of a date and time to allow selection thereof. In another embodiment, the trends window 310 can include a calendar feature configured to allow a user to scroll through dates and times to select a specific date and time. In yet another embodiment, the trends window 310 can include a trend preferences button (not shown) configured to be activated to allow adjustment of a selected time within the trend time period, such as by providing a preferences window in which start and end dates and times of the trend time period can be selected. As in the illustrated embodiment, the trends window 310 can have a movable time marker displayed thereon that can be configured to be movable on the display screen 300 so as to select a date and time within the trend time period.

The time marker can have a variety of configurations. In the illustrated embodiment, the time marker includes a scroll bar 309 configured to be movable along the timeline 307. The timeline 307 is positioned below all of the graphical displays 348, 352, 374, 378 shown in the trends window 310, but the timeline 307 can be in other positions, e.g., above the graphical displays, between adjacent graphical displays, etc. The scroll bar 309 is in the form of a slidable solid line in the illustrated embodiment but can have other forms, e.g., a slidable dotted line, an arrow and/or other symbol adjacent the graphical displays, etc. Start and end dates and times of the timeline 307 can be defined by start and end dates and times of the trend time period. In the illustrated embodiment, the timeline 307 starts at 12:05:00 on 20/09/20 and spans eight hours (the selected trend time period) to 20:05:00 on 20/09/20. A position of the scroll bar 309 along the timeline 307 can define the selected date and time. In the illustrated embodiment, the selected date is 20/09/20 and the selected time is 14:21:10.

In an exemplary embodiment, the scroll bar 309 can be configured to be movable along each of the trendlines 348t, 352t, 374t, 376t currently shown in the graphical displays 348, 352, 374, 378 of the trends window 310. The scroll bar 309 can be configured to move simultaneously along each of the displayed trendlines 348t, 352t, 374t, 376t. The slidable line 309 can thus indicate a selected position along each of the displayed trendlines 348t, 352t, 374t, 376t at the selected date and time. The scroll bar 309 can thus be configured to select a same specific date and time for each of at least the displayed physiological parameters such that data for each of at least the displayed physiological parameters at the selected date and time can be provided on the display screen 300. The display screen 300 can thus be configured to provide a snapshot of the patient's condition at the selected date and time.

The scroll bar 309 can be movable along the timeline 307 in a variety of ways. For example, the scroll bar 309 can be configured to be selected, e.g., by touch on the touchscreen, and moved on the screen 300 by user touch gesture. For another example, the scroll bar 309 can be configured to be selected, e.g., by touch on the touchscreen, at a controller portion 309c thereof. The controller portion 309c can be positioned along the timeline 307 and slidable therealong in a drag and drop fashion so as to move the scroll bar 309 through the timeline 307 and across the displayed trendlines 348t, 352t, 374t, 376t. The scroll bar 309 can be movable in other ways, such as by being selectable along any portion thereof via touchscreen or pointer device and dragged and dropped along the timeline 307, by entering a date and time into a text entry box and thereby causing the scroll bar 309 to move to that date and time along the timeline 307, etc.

Various types of data can be provided regarding each of the physiological parameters at the selected date and time, e.g., at the date and time indicated by the position of the scroll bar 309. In an exemplary embodiment, the trends window 310 can include any one or more of a detail trends window, an assessment window, and a notification window to be displayed at the selected date and time. Each of the detail trends window, the assessment window, and the notification window are discussed in further detail below.

The detail trends window can be configured to show information for one or more physiological parameters in a detail time period surrounding the selected date and time. In an exemplary embodiment, the detail time period can less than the trend time period, e.g., one minute, five minutes, a single heartbeat, three heartbeats, ten minutes, etc., although virtually any time period can be used as the detail time period. The detail time period can thus show a more detailed portion of a trendline during a time period that includes the selected date and time. Similar to that discussed above regarding the current time period, the detail time period can be a predetermined amount of time that can be a default, preprogrammed time period, e.g., preprogrammed into a processor, or can be customized for a particular patient. The detail time period can be adjustable, also similar to that discussed above with respect to the current time period. The detail time period can be customized and/or adjusted in a variety of ways, e.g., by activating a main menu button (not shown) to cause a preferences window to be provided in which the detail time period can be customized and/or adjusted.

The detail trends window can be configured to be shown on the display screen 300 in a variety of ways. In an exemplary embodiment, all available detail trends windows for physiological parameters having graphical displays on the trends window 310 can be displayed for the date and time defined by the scroll bar's position within the trend time period upon activation of the detail time period button 336, e.g., by touching the button 336 on the touchscreen. Additionally or alternatively, the detail trends window for a selected one of the physiological parameters can be shown on the display screen 300 by selecting the trendline for the selected one of the physiological parameters at a location of the scroll bar 309 along that parameter's trendline. Each of the displayed trendlines 348*t*, 352*t*, 374*t*, 376*t* can include a details icon 348*i*, 352*i*, 374*i*, 376*i* thereon at the location of the scroll bar 309 therealong. The details icons 348*i*, 352*i*, 374*i*, 376*i* in the illustrated embodiment each include a circle on the scroll bar 309, but the details icons 348*i*, 352*i*, 374*i*, 376*i* can have any of a variety of configurations, e.g., an "x" and/or other symbol on the scroll bar 309, a "details" button on the screen 300 adjacent each of the graphical displays that can be configured to be selected to show the detail trends window for its associated trendline, a master "details" button on the screen 300 configured to be selected to show the detail trends for each of the displayed trendlines, etc.

Figure 13:
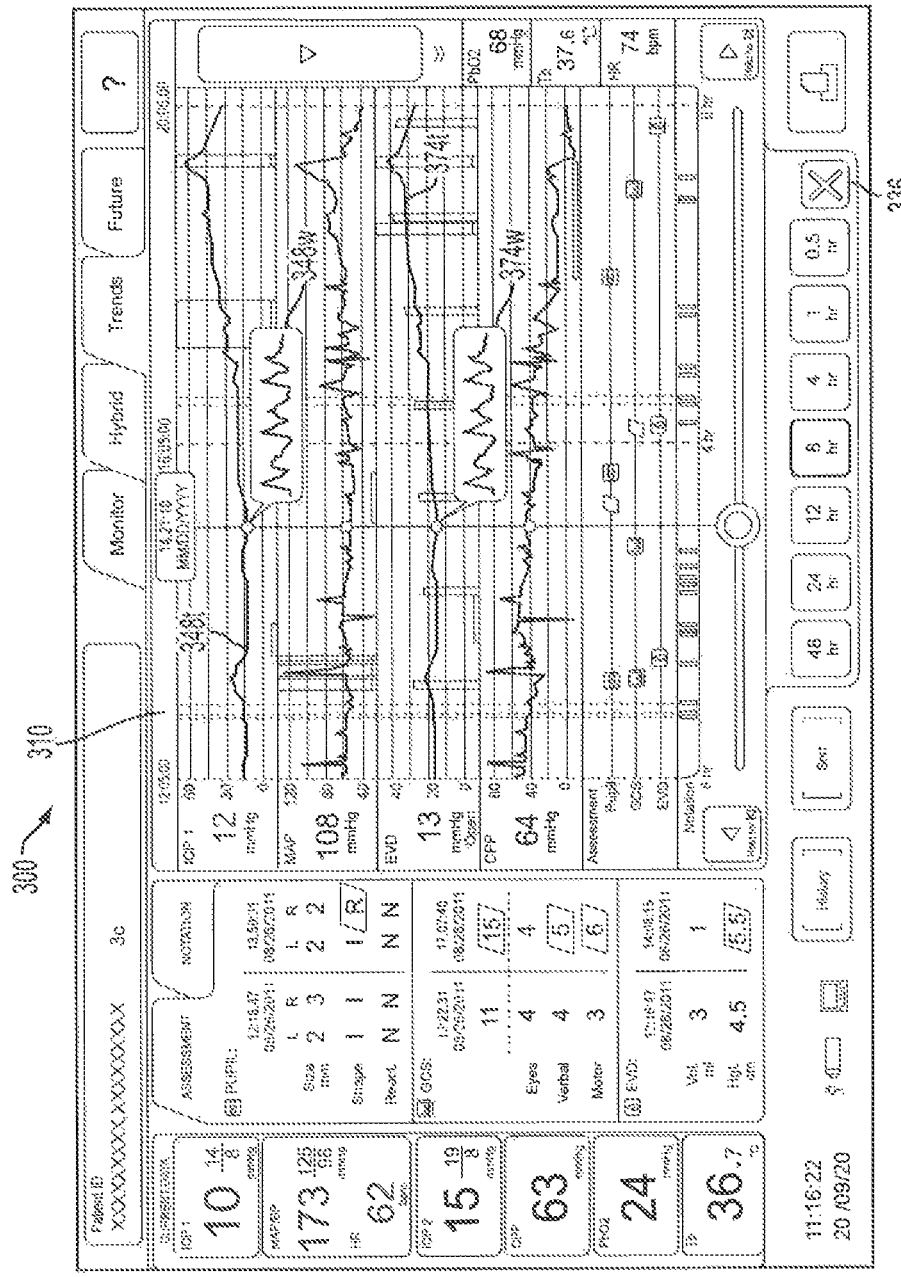
FIG. 13 shows the trends window of FIG. 3 including at least one detail trends window.

FIG. 13 shows an embodiment of the trends window 310 including at least one detail trends window. In the illustrated embodiment, the ICP details icon 348*i* has been selected on FIG. 3 to cause an ICP detail trends window 348*w* to be displayed on the trends window 310, and the EVD details icon 374*i* has been selected on FIG. 3 to cause an EVD detail trends window 374*w* to be displayed on the trends window 310. The detail trends windows 348*w*, 374*w* in the illustrated embodiment each include a zoomed-in view of their respective trendlines 348*t*, 374*w* for the detail trend time period centered at the selected date and time, but the detail trends windows can have a variety of configurations. The detail trends windows 348*w*, 374*w* are displayed on the trends window 310 in the illustrated embodiment, but detail trends window can be configured to be displayed in another window, e.g., a dedicated detail trends window. The detail trends windows 348*w*, 374*w* can be configured to remain displayed on the screen 300 until deselected, e.g., their associated details icons 348*i*, 374*i* are again activated, the detail trends windows 348*w*, 374*w* are dragged and dropped off the screen 300, etc. The detail trends windows 348*w*, 374*w* can be configured to automatically update if the scroll bar 309 is moved while the detail trends windows 348*w*, 374*w* are shown on the screen 300. Alternatively, the detail trends windows 348*w*, 374*w* can be configured to disappear from the screen 300 if the scroll bar 309 is slid along the trendlines 348*t*, 352*t*, 374*t*, 376*t* while the detail trends windows 348*w*, 374*w* are shown on the screen 300.

When all available detail trends windows are shown, e.g., on the trends window 310 or elsewhere, the detail time period button 336 can be configured to be deactivated, e.g., removed from the display screen 300, grayed out (as in the illustrated embodiment), struck out (as in the illustrated embodiment, in which the button 336 is crossed out with an "X"), etc., thereby indicating that no more detail trends windows are available for viewing.

Figure 14:
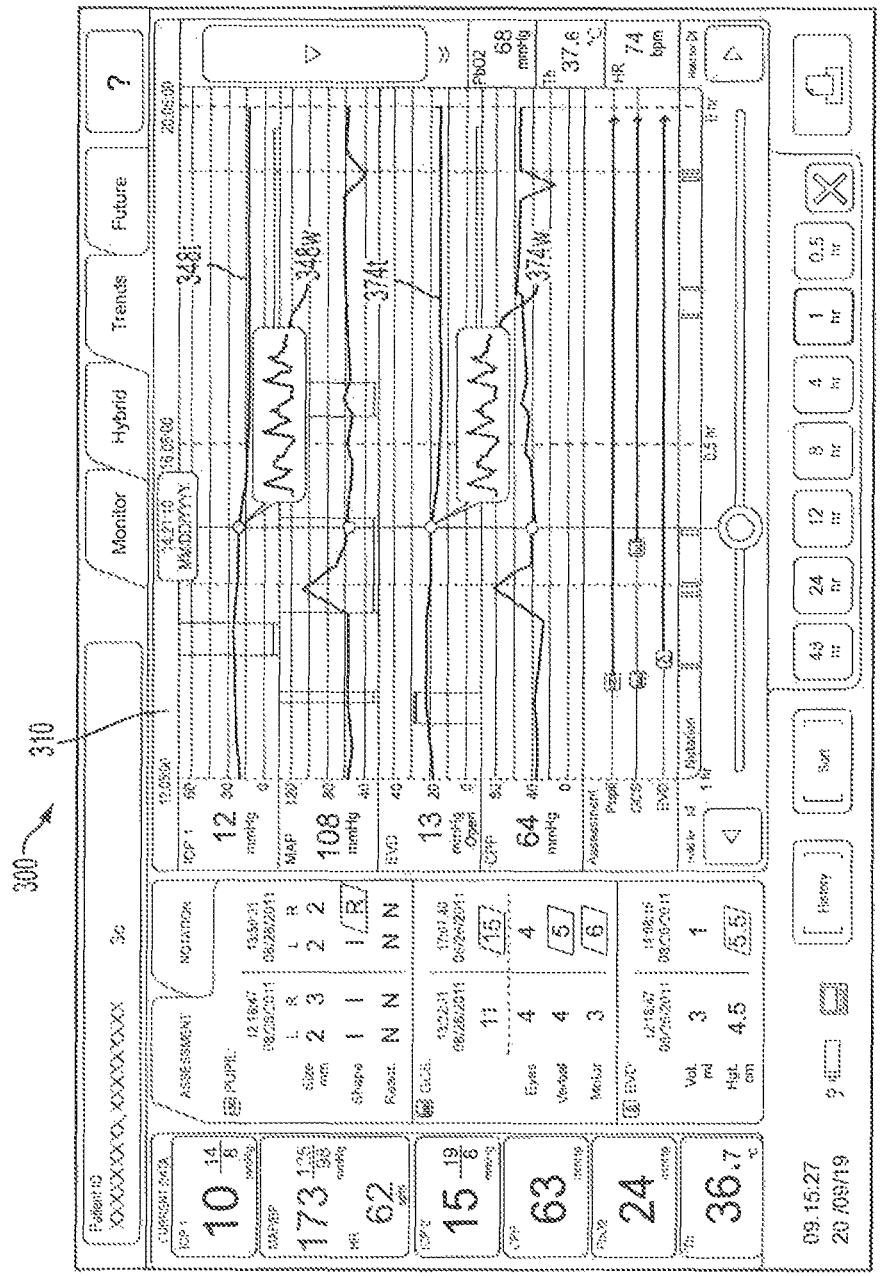
FIG. 14 shows the trends window of FIG. 10 including at least one detail trends window.
Figure 15:
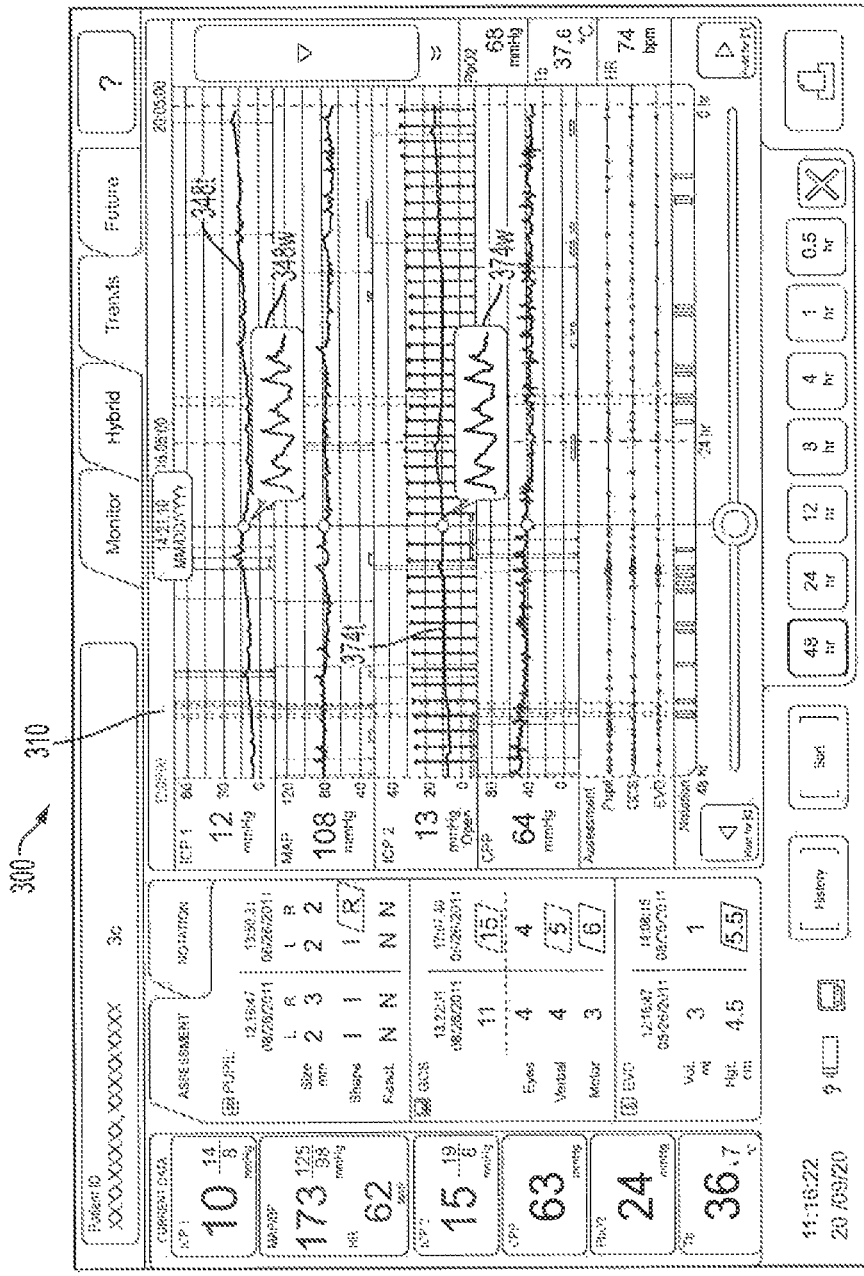
FIG. 15 shows the trends window of FIG. 11 including at least one detail trends window.
Figure 16:
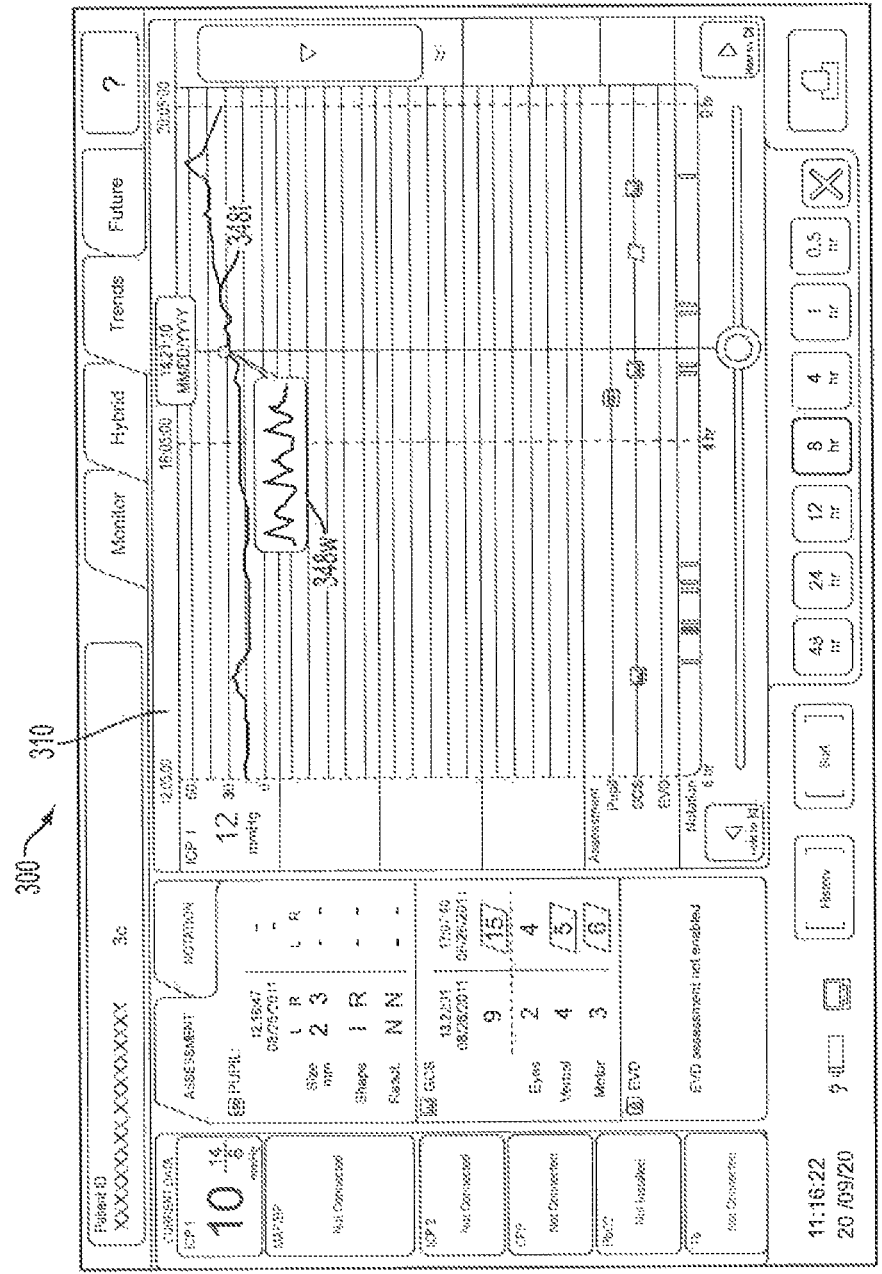
FIG. 16 shows the trends window of FIG. 6 including at least one detail trends window.

FIG. 14 shows an embodiment of the trends window 310 of FIG. 10 after the ICP and EVD details icons 348*i*, 374*i* have been activated so as to cause their associated detail trends windows 348*w*, 374*w* to be shown on the screen 300. FIG. 15 shows an embodiment of the trends window 310 of FIG. 11 after the ICP and EVD details icons 348*i*, 374*i* have been activated so as to cause their associated detail trends windows 348*w*, 374*w* to be shown on the screen 300. FIG. 16 shows an embodiment of the trends window 310 of FIG. 6 after the ICP detail icons 348*i* has been activated so as to cause its associated detail trends window 348*w* to be shown on the screen 300.

The assessment window can be configured to show assessment information regarding one or more diagnostic parameters for the patient at and/or surrounding the selected date and time. Examples of diagnostic parameters include pupil reading, Glasgow Coma Scale (GCS), EVD level, Acute Physiology and Chronic Health Evaluation (APACHE), Simplified Acute Physiology Score (SAPS), Paediatric Index of Mortality (PIM2), Sequential Organ Failure Assessment (SOFA) score, Cancer Mortality Model (CMM), Mortality Prediction Model (MPM), Risk, Injury, Failure, Loss and End-stage (RIFLE) kidney classification, Child-Pugh (CP), Ranson score, Multiple Organ Dysfunction Score (MODS), and Logistic Organ Dysfunction System (LODS). In a neurological context, exemplary diagnostic parameters include pupil reading, GCS, and EVD level.

The display screen 300 can be configured to show an assessment graphical display 351 that corresponds to the trend time period and that includes assessment information in graphical form for the one or more diagnostic parameters. The assessment graphical display 351 is shown positioned below all of the visible physiological parameter graphical displays 348, 352, 374, 378 on the trends window 310 in the illustrated embodiment of FIG. 3, but the assessment graphical display 351 can be positioned above all of the visible physiological parameter graphical displays 348, 352, 374, 378 or positioned between two of the visible physiological parameter graphical displays 348, 352, 374, 378.

The assessment graphical display 351 can be configured to show diagnostic parameter assessment information in graphical or pictorial form. The diagnostic parameters in the illustrated embodiment include pupil reading, GCS, and EVD level, but as mentioned above, any one or more diagnostic parameters can be tracked for a patient. In an exemplary embodiment, each of the available diagnostic parameters can include a graph line 335*g*, 339*g*, 341*g* for each of the pupil reading, GCS, and EVD level diagnostic parameters that extends through the trend time period. The scroll bar 309 can be configured to be movable along each of the graph line 335g, 339g, 341g, similar to that discussed above regarding the trendlines 348t, 352t, 374t, 376t currently shown in the graphical displays 348, 352, 374, 378 of the trends window 310. The scroll bar 309 can thus be configured to move simultaneously along each of the graph lines 335g, 339g, 341g and the displayed trendlines 348t, 352t, 374t, 376t. The slidable line 309 can thus indicate a selected position along each of the displayed graph lines 335g, 339g, 341g and the displayed trendlines 348t, 352t, 374t, 376t at the selected date and time.

Each of the graph lines 335g, 339g, 341g can include assessment markers therealong. Each of the assessment markers can indicate a point within the trend time period, e.g., a specific date and time within the trend time period shown on the trends window 310, that corresponds to a time that the patient was assessed with respect to the assessment marker's associated diagnostic parameter. In other words, each of the assessment markers can indicate a point within the trend time period at which assessment information was received by the system for its associated diagnostic parameter. In the illustrated embodiment, the pupil reading graph line 335g has four assessment markers therealong, the GCS graph line 339g has four assessment markers therealong, and the EVD level graph line 341g has three assessment markers therealong.

The assessment markers can have a variety of configurations. Examples of the assessment markers include icons, geometric shapes, symbols, numbers, letters, alphanumeric characters, etc. In an exemplary embodiment, each of the diagnostic parameters can have its own unique assessment marker. Unique assessment markers can facilitate quick visual distinction between different assessment markers that can be simultaneously shown on the trends screen 310. In the illustrated embodiment of FIG. 3, the unique assessment markers for pupil reading include icons with an eye graphic, the assessment markers for GCS include icons with a line graph graphic, and the assessment markers for EVD level include icons with a fluid drop graphic. In the trend time period shown in FIG. 3, the pupil reading graph line 335g has three eye graphic icon assessment markers therealong, the GCS graph line 339g has three line graph icon assessment markers therealong, and the EVD level graph line 341g has three fluid drop icon assessment markers therealong.

One or more assessment markers can be provided that are common to all of the diagnostic parameters. In an exemplary embodiment, each of the diagnostic parameters can share a common assessment marker configured to indicate a change in a diagnostic parameter. The common assessment marker can have a different color than the unique assessment markers, which can facilitate visual detection of the change. Alternatively, each of the diagnostic markers can include a unique assessment marker configured to indicate a change in the diagnostic marker. In the illustrated embodiment, each of the diagnostic parameters can share a common assessment marker in the form of a parallelogram shape having a bright yellow color, although as mentioned above, other shapes and colors can be used. In the trend time period shown in FIG. 3, the pupil reading graph line 335g has one change assessment markers therealong, the GCS graph line 339g has one change assessment markers therealong, and the EVD level graph line 341g has zero change assessment markers therealong.

FIGS. 5, 6, and 16 illustrate embodiments in which at least one diagnostic parameter does not include any assessment markers in the presently selected trend time period, which is the EVD graph line 341g in these embodiments.

One or more diagnostic parameters may not have available information for a variety of reasons, such as no diagnostic information being gathered at all or gathered during the selected time period.

The diagnostic parameter assessment information, pupil reading information, GCS information, EVD level information, etc., can be received by the system in a variety of ways. In an exemplary embodiment, the display screen 300 can be configured to provide user access to a diagnostic parameter entry screen (not shown) configured to allow a user to manually enter diagnostic parameter assessment information and associate a date and time therewith, e.g., a date and time that the information was gathered by medical personnel. The diagnostic parameter entry screen can have a variety of configurations, as will be appreciated by a person skilled in the art, such as by providing a text entry box, a drop-down menu of diagnostic parameter options, etc. Various embodiments of entering information into a system via a user interface are described in further detail in U.S. Pat. Pub. No. 2009/0005703 entitled "Medical Monitor User Interface" filed Jun. 27, 2007.

The assessment markers can be configured to be automatically provided in the assessment graphical display 351 for the diagnostic parameters along their associated graph lines 335g, 339g, 341g. In other words, if the system has one or more diagnostic parameter assessment information, e.g., stored in a memory thereof, that falls within the currently selected trend time period, assessment marker(s) for that diagnostic parameter assessment information can be automatically provided on the appropriate ones of the graph lines 335g, 339g, 341g.

The display screen 300 can be configured to show the assessment graphical display 351 simultaneously with an assessment window 333. The assessment window 333 can be configured to provide the data associated with the assessment markers in the assessment graphical display 351. In other words, the assessment window 333 can provide the numerical, text, and/or other clinically relevant data associated with the diagnostic parameters.

The assessment window 333 can be configured to be shown on the display screen 300 in a variety of ways. In an exemplary embodiment, assessment information for each available diagnostic parameter can be displayed in the assessment window 333 for the date and time defined by the scroll bar's position within the trend time period and along each of the diagnostic parameter's graph lines 335g, 339g, 341g. The diagnostic parameter(s) can have information available at the selected date and time, but in some instances, diagnostic information may not have been received by the system at exactly the selected date and time. The assessment window 333 can thus be configured to show information at the selected date and time and/or at dates/times adjacent to the selected date and time, e.g., before and/or after the selected date and time. The assessment window 333 can be configured to show assessment information for a diagnostic parameter at a nearest date and time before the selected date and time at which information was received for the diagnostic parameter and/or to show assessment information for a diagnostic parameter at a nearest date and time after the selected date and time at which information was received for the diagnostic parameter.

In an exemplary embodiment, the assessment window 333 can be configured to concurrently show assessment information for each diagnostic parameter being tracked, gathered, etc. for the patient. In this way, the assessment window 333 can provide a complete picture of the patient's diagnostic assessment. If more diagnostic parameters are available than can be shown at a single time, the assessment window 333 can include a scroll element, similar to that discussed above. If a plurality of diagnostic parameters are available, an order in which the diagnostic parameters are displayed within the assessment window 333 can be adjusted, similar to that discussed above regarding adjustment of the order of graphical displays within the trends window 310. In another embodiment, the assessment window 333 can be configured to show only assessment information for one diagnostic parameter at a time, with each diagnostic parameter being selectable for display, e.g., by activation of an assessment button (not shown).

The assessment window 333 can be configured to be displayed concurrently with the trends window 310. The display screen 300 can thus provide a fuller snapshot of the patient's condition. The assessment window 333 can, however, be configured to be displayed separately from the trends window 310, e.g., in its own dedicated window.

The assessment window 333 can be configured to be displayed automatically with the trends window 310, e.g., when the trends tab 306 is selected by a user, whether or not any assessment information is available at and/or adjacent to the selected date and time. Alternatively, the assessment window 333 can be configured to be displayed in response to a user input request for assessment information, e.g., by activating an assessment button (not shown) on the display screen 300, by selecting an assessment tab 343 on the trends window 310, etc.

In the illustrated embodiment of FIG. 3, the assessment window 333 includes pupil reading assessment information 335, GCS assessment information 339, and EVD level assessment information 341. However, as mentioned above, any one or more diagnostic parameters can be shown in an assessment window. None of the diagnostic parameters have assessment information associated therewith at the selected date and time within the trend time window in the illustrated embodiment. The assessment window 333 thus shows assessment information for each diagnostic parameter at a nearest date and time before the selected date and time at which information was received for the diagnostic parameter and shows assessment information for a diagnostic parameter at a nearest date and time after the selected date and time at which information was received for the diagnostic parameter.

The assessment window 333 in the illustrated embodiment is displayed concurrently with the trends window 310, but as mentioned above, the assessment window 333 can be otherwise displayed. The assessment tab 343 is selected in the embodiment shown in FIG. 3 such that the assessment window 333 is shown. One or more other parameter information windows can be selected and shown, e.g., a notification window that can be selected via a notification tab 349.

The notification window can be configured to show notification information regarding one or more medically-related events that occurred as related to the patient and/or surrounding the selected date and time. By being configured to provide notification of medically-related events, the display screen 300 can allow a user viewing the screen 300 to more easily determine why one or more physiological parameters and/or diagnostic parameters may have changed at a certain point or during a certain period of time. In other words, the occurrence of a medically-related event can help inform why a particular parameter changed at a certain time. In general, medically-related events include events that can affect one or more physiological parameters. General examples of medically-related events include interventions (e.g., actions performed by medical personnel as related to the patient such as medication administration, adjustment of EVD, administration of oxygen, etc.), planned or unplanned events (e.g., spontaneously occurring or purposefully occurring events that happened to the patient, such as a seizure, an MRI image being taken, providing a meal, etc.), and notes (e.g., information noted by medical personnel as potentially having importance in the patient's treatment and care such as movement of the patient to another area of the hospital). Examples of medically-related events include the administration of a medication by a caregiver, the adjustment of a sensing device that monitors ICP and/or other physiological parameter, taking the patient's temperature, caregiver observations, moving the patient to another room, transporting the patient, reactivity, cleaning the patient, taking an MRI or other scan of the patient, the patient eating, the patient having a family/friend visitor, oxygen challenge, the patient being awake or asleep, etc. For example, notification information indicating that a patient received a drug at a particular time can facilitate a medical practitioner's assessment as to whether the drug had the desired clinical effect based on trends of one or more physiological parameters following the particular time. For another example, in a neurological context, any movement of the patient can affect ICP such that notification information providing notice that a patient was taken for an MRI at a certain time could help explain a change in ICP measurement values at and/or after the certain time.

Figure 17:
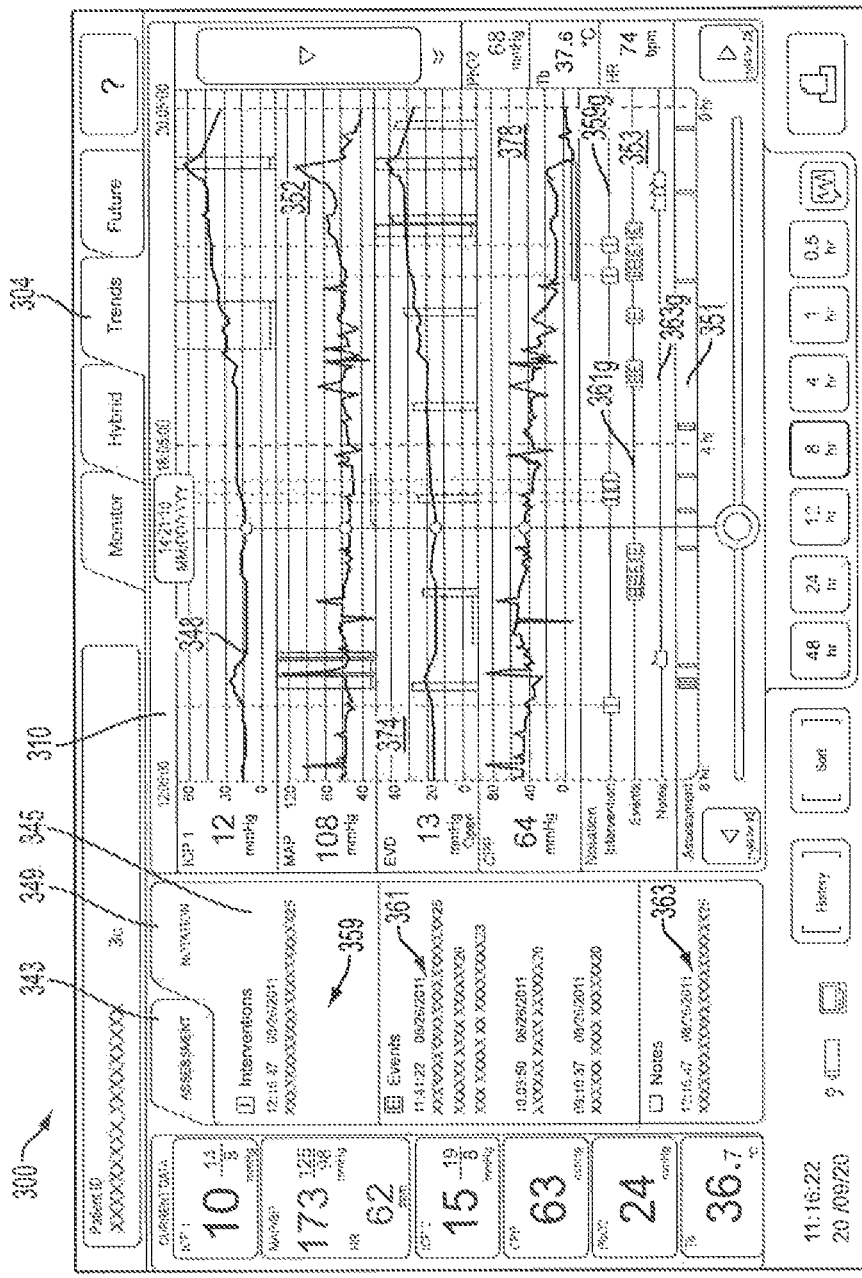
FIG. 17 shows the trends window of FIG. 3 including the trends information, the current data over a current period of time for the plurality of physiological parameters, and notification information over the trends period of time.

The display screen 300 can be configured to show the notification graphical display 353 that corresponds to the trend time period and that includes notification information in graphical form for the one or more diagnostic parameters. FIG. 17 illustrates an embodiment of the notification graphical display 353 when the notification tab 349 has been selected. The notification graphical display 353 is shown positioned below all of the visible physiological parameter graphical displays 348, 352, 374, 378 and above the assessment graphical display 351 on the trends window 310 in the illustrated embodiment of FIG. 17, but the notification graphical display 353 can be positioned above or below any one or more of the visible physiological parameter graphical displays 348, 352, 374, 378 and the assessment graphical display 351.

The notification graphical display 353 can be configured to show notification information in graphical or pictorial form. The notification information in the illustrated embodiment includes interventions, unplanned events, and notes, but as mentioned above, any notification information can be provided. Each of the interventions, unplanned events, and notes can include a plurality of different types of notifications that fall under its associated general category of interventions, unplanned events, and notes. In an exemplary embodiment, each of the available medically-related events can include a graph line 359g, 361g, 363g for each of the interventions, unplanned events, and notes medically-related events that extend through the trend time period. The scroll bar 309 can be configured to be movable along each of the graph line 359g, 361g, 363g, similar to that discussed above regarding the graph lines 335g, 339g, 341g and the trendlines 348t, 352t, 374t, 376t. The scroll bar 309 can thus be configured to move simultaneously along each of the graph lines 359g, 361g, 363g and the displayed trendlines 348t, 352t, 374t, 376t. The slidable line 309 can thus indicate a selected position along each of the displayed graph lines 359g, 361g, 363g and the displayed trendlines 348t, 352t, 374t, 376t at the selected date and time.

Each of the graph lines 359g, 361g, 363g can include notification markers therealong. The notification markers can generally be configured similar to the assessment markers discussed above. Each of the notification markers can indicate a point within the trend time period, e.g., a specific date and time within the trend time period shown on the trends window 310, that corresponds to a time that a medically-related event occurred with respect to the patient. In other words, each of the notification markers can indicate a point within the trend time period at which notification information was received by the system for its associated medically-related event. In the illustrated embodiment of FIG. 17, the intervention graph line 359g has five notification markers therealong, the events graph line 361g has thirteen notification markers therealong, and the notes graph line 363g has four notification markers therealong.

The notification markers can have a variety of configurations. Examples of the notification markers include icons, geometric shapes, symbols, numbers, letters, alphanumeric characters, etc. In an exemplary embodiment, each of the medically-related events can have its own unique notification marker. However, one or more notification markers can be provided that are common to all of the medically-related events. Unique notification markers can facilitate quick visual distinction between different notification markers that can be simultaneously shown on the trends screen 310. In the illustrated embodiment of FIG. 3, the unique notification markers for interventions include icons labeled "I," the notification markers for events include icons labeled "E," and the notification markers for notes include word bubble symbols. One or more of the graph lines 359g, 361g, 363g can lack any notification markers for a given trend time period, e.g., because no medically-related events occurred during that time period.

The notification information can be received by the system in a variety of ways. In an exemplary embodiment, the display screen 300 can be configured to provide user access to a notification information entry screen (not shown) configured to allow a user to manually enter notification information and associate a date and time therewith, e.g., a date and time that the information was gathered by medical personnel. The notification information entry screen can have a variety of configurations, as will be appreciated by a person skilled in the art, such as by providing a text entry box, a drop-down menu of diagnostic parameter options, etc. As mentioned above, various embodiments of entering information into a system via a user interface are described in further detail in U.S. Pat. Pub. No. 2009/0005703 entitled "Medical Monitor User Interface" filed Jun. 27, 2007. The notification information can be configured to be automatically provided, such as for unplanned or planned events sensed by a sensing device, e.g., opening or closing of an EVD, when EVD pressure is measured and an ICP sensing device is exposed, triggering of an alarm or a goal alarm, etc.

The notification markers can be configured to be automatically provided in the notification graphical display 353 for the medically-related events along their associated graph lines 359g, 361g, 363g. In other words, if the system has one or more notification information, e.g., stored in a memory thereof, that falls within the currently selected trend time period, notification marker(s) for that notification information can be automatically provided on the appropriate ones of the graph lines 359g, 361g, 363g.

The display screen 300 can be configured to show the notification graphical display 353 simultaneously with a notification window 345. The notification window 345 can be configured to provide the data associated with the assessment markers in the notification graphical display 353. In other words, the notification window 345 can provide the numerical, text, and/or other clinically relevant data associated with the medically-related events.

The notification window 345 can be configured to be shown on the display screen 300 in a variety of ways. In an exemplary embodiment, notification information for each available medically-related event can be displayed in the notification window 345 for the date and time defined by the scroll bar's position within the trend time period and along each of the graph lines 359g, 361g, 363g. The medically-related event(s) can have information available at the selected date and time, but in some instances, notification information may not have been received by the system at exactly the selected date and time. The notification window 345 can thus be configured to show information at the selected date and time and/or at dates/times adjacent to the selected date and time, e.g., before and/or after the selected date and time. The notification window 345 can be configured to show notification information for a medically-related event at a nearest date and time before the selected date and time at which information was received for the medically-related event and/or to show notification information for a medically-related event at a nearest date and time after the selected date and time at which information was received for the medically-related event.

In an exemplary embodiment, the notification window 345 can be configured to concurrently show notification information for each medically-related event regarding the patient. In this way, the notification window 345 can provide a complete picture of the patient's treatment and care. If more medically-related events are available than can be shown at a single time, the notification window 345 can include a scroll element, similar to that discussed above. If a plurality of medically-related events are available, an order that the medically-related events are displayed within the notification window 345 can be adjusted, similar to that discussed above regarding adjustment of the order of graphical displays within the trends window 310. In another embodiment, the notification window 345 can be configured to show only notification information for one medically-related event at a time, with each medically-related event being selectable for display, e.g., by activation of a notification button (not shown).

The notification window 345 can be configured to be displayed concurrently with the trends window 310. The display screen 300 can thus provide a fuller snapshot of the patient's condition. The notification window 345 can, however, be configured to be displayed separately from the trends window 310, e.g., in its own dedicated window.

The notification window 345 can be configured to be displayed automatically with the trends window 310, e.g., when the trends tab 306 is selected by a user, whether or not any notification information is available at and/or adjacent to the selected date and time. Alternatively, the notification window 345 can be configured to be displayed in response to a user input request for notification information, e.g., by activating a notification button (not shown) on the display screen 300, by selecting the notification tab 349 on the trends window 310, etc.

In the illustrated embodiment of FIG. 3, the notification window 345 includes interventions information 359, events information 361, and notes information 363. However, as mentioned above, any one or more medically-related events can be shown in a notification window. None of the medically-related events have notification information associated therewith at the selected date and time within the trend time window in the illustrated embodiment. The notification window 345 thus shows notification information for each medically-related event at a nearest date and time before the selected date and time at which information was received for the medically-related event and shows notification information for a medically-related event at a nearest date and time after the selected date and time at which information was received for the medically-related event.

The notification window 345 in the illustrated embodiment is displayed concurrently with the trends window 310, but as mentioned above, the notification window 345 can be otherwise displayed. The assessment tab 349 is selected in the embodiment shown in FIG. 17 such that the notification window 345 is shown.

When the notification tab 349 is selected, the assessment window 333 and the assessment graphical display 351 can be configured to be removed from the display screen 300 or minimized on the display screen 300. Similarly, when the assessment tab 343 is selected, a notification window 357 and the notification graphical display 353 can be configured to be removed from the display screen 300 or minimized on the display screen 300. In the illustrated embodiment of FIG. 3, the notification graphical display 353 is minimized on the display screen 300 when the assessment tab 343 is selected. The minimized notification graphical display 353 can still include notification markers thereon, as shown in the illustrated embodiment. A user viewing the display screen 300 can thus receive at least some notification information despite the notification tab 349 not being selected. The user can thus better decide whether to access the notification information. In the illustrated embodiment of FIG. 17, the assessment graphical display 351 is minimized on the display screen 300 when the notification tab 349 is selected. The minimized assessment graphical display 351 can still include assessment markers thereon, as shown in the illustrated embodiment. A user viewing the display screen 300 can thus receive at least some assessment information despite the assessment tab 343 not being selected. The user can thus better decide whether to access the assessment information.

Figure 18:
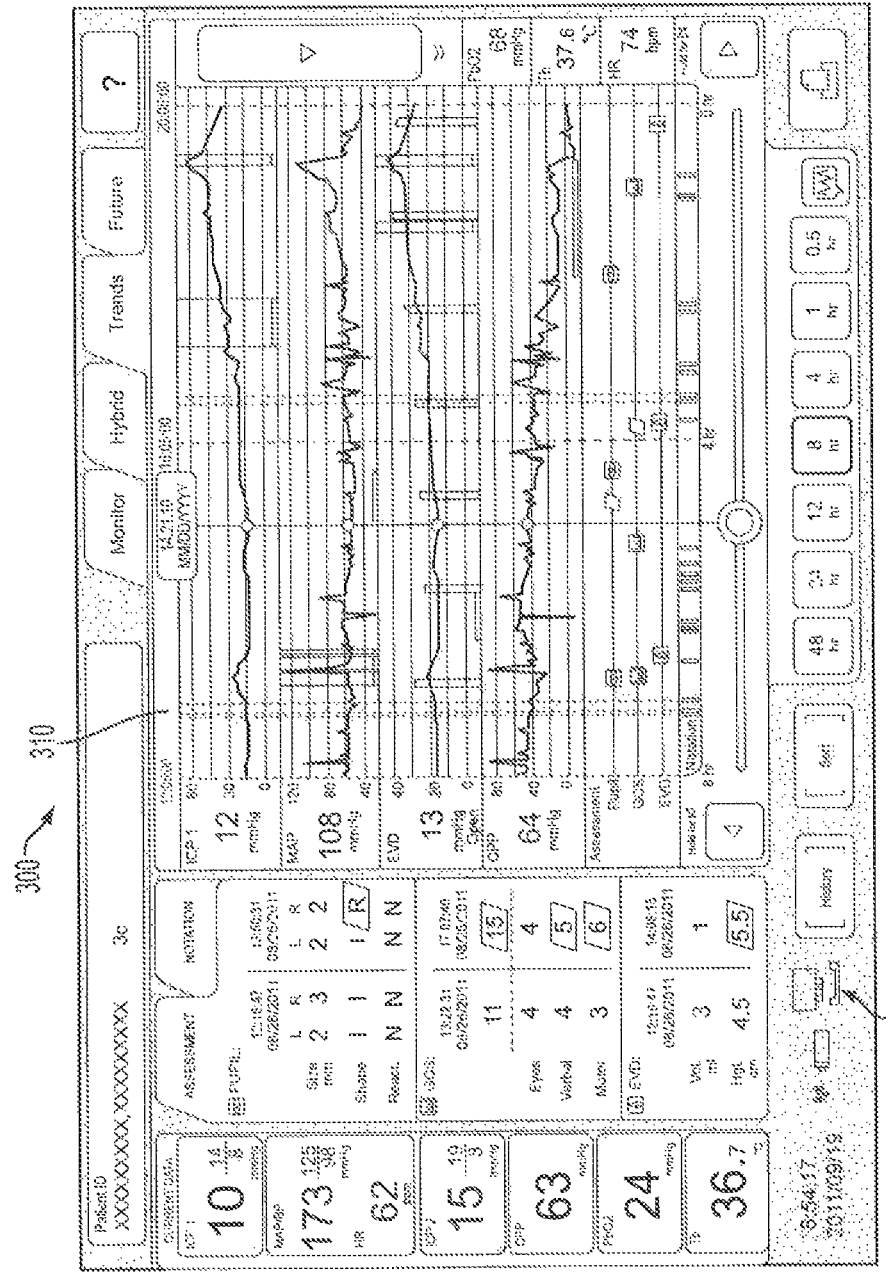
FIG. 18 shows the trends window of FIG. 3 when the medical monitoring system is undocked.

FIG. 18 shows an embodiment of the trend window 310 of FIG. 3 when the device is undocked, e.g., is running from an on-board power supply such as a battery. The undocked state of the device can be indicated in any one or more ways, such as by changing a background color of the display screen 300 (e.g., from black in FIG. 3 to yellow in FIG. 18, changing the docking indicator 372 (e.g., from a docked icon in FIG. 3 to an undocked icon in FIG. 18), a textual identifier (not shown) (e.g., "UNDOCKED", etc.), etc. Providing clear notice of the device being undocked can help prevent the device from running out of power, going out of range, etc.

As mentioned above, selection of the monitor tab 302 on the display screen 300 can cause a monitor window (not shown) to be shown on the screen 300. The monitor window can be configured to show information for one or more physiological parameters in the current time period. The monitor window can be configured to show information for one or more physiological parameters in the current time period, e.g., the time period for the current data window 312 of the trends screen 310. In general, the monitor window can show information similar to the information provided in the current data window 312. In an exemplary embodiment, the monitor window can provide more information than the information available in the current data window 312.

For each of the physiological parameters, the monitor window can be configured to show a textual display of parameter information for the current time period and/or a graphical display of parameter information for the current time period. The graphical display can represent a parameter graphically with a graph line plotted over the current time period. However, virtually any graphical representation can be used, such as a graph line, a bar graph, a plot of discrete data points, and/or other pictorial display. The textual display can represent a parameter textually and/or pictorially. In an exemplary embodiment, the textual display can include information related to an average of the parameter values gathered and/or calculated during the current time period including a current average (e.g., the current average intracranial pressure), a current actual value (e.g., a most recently measured and/or calculated ICP value), a normal range for the current average, and a goal range for the current average. The textual display can, however, display one or more current values in addition to or instead of the current average. Various embodiments of monitor windows are described in further detail in U.S. Pat. Pub. No. 2009/0005703 entitled "Medical Monitor User Interface" filed Jun. 27, 2007.

As mentioned above, selection of the hybrid tab 304 on the display screen 300 can cause a hybrid window (not shown) to be shown on the screen 300. The hybrid window can be configured to show information for one or more physiological parameters over a current time period and can show information for the one or more physiological parameters over the trend time period. The hybrid window can thus facilitate comparison of current information with previously gathered information, which can facilitate a more long term analysis of the patient's physiological parameters. The information for the one or more physiological parameters over the current time period can include information similar to that discussed above regarding the information that can be shown on the monitor window. The information for the one or more physiological parameters over the other time period can include information similar to that discussed above regarding the information that can be shown on the trends window. The hybrid window can thus be configured as a hybrid of the monitor window and the trends window. The information displayed in the hybrid window for each of the physiological parameters can be based on data received by the monitoring device in any of a variety of ways, as discussed above. For each of the physiological parameters shown on the screen, the hybrid window can be configured to show at least one of a textual display of parameter information for the current time period and a graphical display of parameter information for the current time period, and at least one of a textual display of parameter information for a trend time period and a graphical display of parameter information for the trend time period. Embodiments of hybrid windows are described in further detail in U.S. Pat. Pub. No. 2009/0005703 entitled "Medical Monitor User Interface" filed Jun. 27, 2007.

As mentioned above, selection of the future tab 308 on the display screen 300 can cause a future window (not shown) to be displayed on the screen 300. The future window can show information for one or more physiological parameters in a future time period that is after the current time period. The future time period can be a predetermined amount of time that can be a default, preprogrammed time period, e.g., preprogrammed into a processor, or can be customized for a particular patient. The future time period can be, e.g., in a range of about five to sixty seconds, in a range of about five to ten seconds, a single heartbeat, a few heartbeats of the patient, etc. The future time period can be adjustable similar to that discussed above, such as when a user activates a preferences menu or soft button. Adjustment of the future time period can allow for various clinical protocols, as such protocols can require tracking of a parameter over different time periods.

Any one or more physiological parameters can be shown on the future window. The information displayed for each of the physiological parameters can be based on data received by the monitoring device in any of a variety of ways, as discussed above. For each of the physiological parameters, the future window can be configured to show a textual display of parameter information for the future time period and/or a graphical display of parameter information for the future time period, similar to the textual and graphical displays discussed above. Which one or more of the physiological parameters have a textual display only, have a graphical display only, or have both a textual display and a graphical display can be user-adjusted, such as by dragging and dropping displays on the touchscreen or activating a preferences menu or soft button. The future data can be shown in the future window in any one or more ways, such as by scatter plots, spider plots, plotting one parameter against another, plotting one parameter against another within a specific period of time, 3D plot (where the third axis is time).

The parameter information shown on the future window can be based on analysis of actual parameters values gathered from the patient. In other words, the information for a physiological parameter in the future time period can include projections of future parameter values based on actual values of that parameter gathered from the patient. Future parameter values for a physiological parameter can be extrapolated from the actual values gathered from the patient for that parameter using any one or more extrapolation techniques, as will be appreciated by a person skilled in the art. Examples of extrapolation techniques include linear extrapolation, linear extrapolation, conic extrapolation, and polynomial extrapolation. Various software known in the art can be used to perform such extrapolation, such as Fityk (available under GNU General Public License), Ch (marketed by SoftIntegration, Inc. of Davis, Calif.), Zun-Zun.com (online curve fitting), and savetman.com (online curve fitting using least squares fit with weights). The future data can be correlated (e.g., autocorrelated and/or cross correlated) and/or the future data can be manipulated for frequency analysis.

FIGS. 3-18 are directed to user interfaces in a neurological context, e.g., for use in monitoring a patient with a traumatic brain injury. However, the methods, systems, and devices described herein are applicable in other medical contexts and can be used in monitoring a patient having virtually any ailment(s). Also, while FIGS. 3-18 use ICP, MAP/BP, HR, EVD ICP, CPP, PbO2, and Tb, as exemplary physiological parameters, this is by way of illustration only. The methods, systems, and devices described herein can be applied to virtually any physiological parameters of a patient.

Any of the methods described herein can be performed by executing a program. The program can be stored on a computer readable medium, such as compact disc, a diskette, a memory device, etc.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system, comprising:
a display screen; and
a processor configured to:
receive a plurality of values for each of a plurality of physiological parameters measured from a patient over a period of time using a plurality of sensing devices, the plurality of physiological parameters including at least external ventricular drainage (EVD) intracranial pressure (ICP), and the plurality of sensing devices including at least an external fluid coupled sensor configured to measure the EVD ICP and to be connected to an EVD system having the EVD ICP,
cause the display screen to show a current value window that shows a current value for each of the plurality of physiological parameters and that indicates a current state of the EVD, the current state being either the EVD system being open or the EVD system being closed,
cause the display screen to show a trends window that shows a trendline for each of the plurality of physiological parameters, each of the trendlines indicating for its associated physiological parameter the values of the physiological parameter over the period of time,
cause a time marker to be displayed on the trends window, a position of the time marker relative to each of the trendlines indicating a selected time within the period of time, and
cause the display screen to show an assessment window that indicates a value of each of the plurality of physiological parameters at the selected time,
wherein data displayed on at least one of the current value window, the trends window, and the assessment window is usable to at least one of diagnose, treat, and assess the patient.

2. The system of claim 1, wherein the plurality of physiological parameters also includes at least one of ICP, mean arterial blood pressure (MAP), cerebral perfusion pressure (CPP), oxygen saturation ($pO_2$), heart rate, temperature, pressure reactivity index (PRx), pressure-volume compensatory reserve (RAP) index, fluid pressure in an implantable restriction device implanted in the patient, flow rate through an implantable valve implanted in the patient, gastric pH level, EEG, and tissue impedance.

3. The system of claim 1, wherein the trends window indicates a state of the EVD.

4. The system of claim 1, wherein the time marker includes a mark crossing each of the trendlines.

5. The system of claim 1, wherein the processor is configured to receive a user input selecting the time, and the marker is movable simultaneously along each of the trendlines based on the user-selected time.

6. The system of claim 1, wherein the processor is configured to:
receive a notification identifying a medically-related event experienced by the patient at a time within the period of time, the medically-related event being an event that affects at least one of the plurality of physiological parameters, and
cause at least one notification marker to be displayed on at least one of the trendlines in response to the receipt of the notification, the notification marker being automatically added at a point on the at least one of the trendlines within the period of time that corresponds to the time at which the patient experienced the medically-related event.

7. A method, comprising:
receiving at a processor a plurality of values for each of a plurality of physiological parameters measured from a patient over a period of time using a plurality of sensing devices, the plurality of physiological parameters including at least external ventricular drainage (EVD) intracranial pressure (ICP), and the plurality of sensing devices including at least an external fluid coupled sensor measuring the EVD ICP and connected to an EVD system having the EVD ICP,
causing, with the processor, a display screen to show a current value window that shows a current value for each of the plurality of physiological parameters and that indicates a current state of the EVD, the current state being either the EVD system being open or the EVD system being closed,
causing, with the processor, the display screen to show a trends window that shows a trendline for each of the plurality of physiological parameters, each of the trendlines indicating for its associated physiological parameter the values of the physiological parameter over the period of time,
causing, with the processor, a time marker to be displayed on the trends window, a position of the time marker relative to each of the trendlines indicating a selected time within the period of time, and
causing, with the processor, the display screen to show an assessment window that indicates a value of each of the plurality of physiological parameters at the selected time,
wherein data displayed on at least one of the current value window, the trends window, and the assessment window is usable to at least one of diagnose, treat, and assess the patient.

8. The method of claim 7, wherein the plurality of physiological parameters also includes at least one of ICP, mean arterial blood pressure (MAP), cerebral perfusion pressure (CPP), oxygen saturation ($pO_2$), heart rate, temperature, pressure reactivity index (PRx), pressure-volume compensatory reserve (RAP) index, fluid pressure in an implantable restriction device implanted in the patient, flow rate through an implantable valve implanted in the patient, gastric pH level, EEG, and tissue impedance.

9. The method of claim 7, wherein the trends window indicates a state of the EVD.

10. The method of claim 7, wherein the time marker includes a mark crossing each of the trendlines.

11. The method of claim 7, further comprising receiving at the processor a user input selecting the time, and wherein the marker is movable simultaneously along each of the trendlines based on the user-selected time.

12. The method of claim 7, further comprising:
receiving at the processor a notification identifying a medically-related event experienced by the patient at a time within the period of time, the medically-related event being an event that affects at least one of the plurality of physiological parameters, and
causing, with the processor, at least one notification marker to be displayed on at least one of the trendlines in response to the receipt of the notification, the notification marker being automatically added at a point on the at least one of the trendlines within the period of time that corresponds to the time at which the patient experienced the medically-related event.

* * * * *